US006335027B1

(12) United States Patent
Levy

(10) Patent No.: US 6,335,027 B1
(45) Date of Patent: Jan. 1, 2002

(54) CONTROLLED DELIVERY COMPOSITIONS AND PROCESSES FOR TREATING ORGANISMS IN A COLUMN OF WATER OR LAND

(75) Inventor: Richard Levy, Fort Myers, FL (US)

(73) Assignee: Lee County Mosquito Control District, FL (US)

( * ) Notice: Subject to any disclaimer, the term of this patent is extended or adjusted under 35 U.S.C. 154(b) by 0 days.

(21) Appl. No.: 09/458,045

(22) Filed: Dec. 10, 1999

Related U.S. Application Data

(60) Division of application No. 08/674,813, filed on Jul. 3, 1996, now Pat. No. 6,001,382, which is a continuation-in-part of application No. 08/434,313, filed on May 2, 1995, now Pat. No. 5,698,210, which is a continuation-in-part of application No. 08/409,301, filed on Mar. 24, 1995, now abandoned, which is a continuation-in-part of application No. 08/406,344, filed on Mar. 17, 1995, now abandoned.

(51) Int. Cl.[7] .............................................. A01N 25/34

(52) U.S. Cl. ....................... 424/409; 424/405; 424/406; 424/408; 424/411; 424/410; 424/477; 424/484; 424/485; 424/486; 424/488; 424/489; 424/78.09; 424/84; 424/451; 43/42.06; 119/212; 119/230; 119/231; 119/242; 428/34.1; 428/34.3; 428/36.9; 206/811

(58) Field of Search ................................ 424/405, 408, 424/469, 438, 84, 484–489, 451, 464, 76.8, 78.09, DIG. 8–11; 119/204, 212, 230, 231, 234, 242; 43/42.06, 131; 523/122; 428/34.1, 34.3, 36.9; 206/811; 220/560; 222/DIG. 30, 565; 383/1

(56) References Cited

U.S. PATENT DOCUMENTS 1,419,618 A * 6/1922 Deming ...................... 424/438
3,056,724 A * 10/1962 Marston ..................... 424/438

(List continued on next page.)

FOREIGN PATENT DOCUMENTS

EP 0 453 397 A1 10/1991

(List continued on next page.)

OTHER PUBLICATIONS

Cui et al., “Preparation of Gelling Microspheres of Acebutolol Hydrochloride by Power Coating With Sodium Alginate in the Polymeric Spherical Crystallization System”, Proceed. Intern. Symp. Control. Rel. Bioact, Mater. , 23, 1996, pp. 345–346.

*Primary Examiner*—Neil S. Levy
(74) *Attorney, Agent, or Firm*—Finnegan, Henderson, Farabow, Garrett & Dunner, L.L.P.

(57) ABSTRACT

Controlled release compositions of matter are disclosed comprising complexes for treating a population of one or more aquatic organisms in a column of water. The complexes comprise at least one system wherein the system comprises at least one bioactive agent as a component selected for treating a population of aquatic organisms, at least one carrier component, and at least one coating component for regulating the controlled release rate and release profile of the bioactive agent in water or at least one bioactive agent and one joint-function component that can serve as both a carrier and coating to regulate the controlled release rate and release profile of the bioactive agent in water, with or without optional binder components and/or additional formulation materials. The components are selected to sink or float so that the complexes will permeate and/or remain in any planar or volumetric segment of a water column for a period of time that is sufficient to effectively treat a population of aquatic organisms. Methods for treating a column of water are also disclosed which comprises delivering the compositions to a column of water or to a dry preflood area (pretreatment) that will develop in a column of water or a flood area. The composition and process can also be used to treat terrestrial organisms.

69 Claims, 1 Drawing Sheet

12

10

U.S. PATENT DOCUMENTS

| | | | | | |
|---|---|---|---|---|---|
| 3,119,738 | A | * | 1/1964 | McHolo | 424/438 |
| 3,274,052 | A | | 9/1966 | Yaffe et al. | |
| 3,732,206 | A | | 5/1973 | Kovats | 525/54.31 |
| 3,917,814 | A | | 11/1975 | Hedges et al. | |
| 4,331,652 | A | * | 5/1982 | Ludwig et al. | 424/438 |
| 4,374,126 | A | | 2/1983 | Cardarelli et al. | 424/81 |
| 4,379,168 | A | | 4/1983 | Dotolo | 514/763 |
| 4,464,317 | A | | 8/1984 | Thies et al. | |
| 4,818,534 | A | | 4/1989 | Levy | |
| 4,824,675 | A | * | 4/1989 | Wong et al. | 424/438 |
| 4,971,796 | A | | 11/1990 | Sjogren | |
| 4,983,389 | A | | 1/1991 | Levy | |
| 4,983,390 | A | | 1/1991 | Levy | |
| 4,985,251 | A | | 1/1991 | Levy | |
| 5,180,585 | A | | 1/1993 | Jacobson et al. | |
| 5,371,109 | A | | 12/1994 | Engstrom et al. | 514/786 |
| 5,412,005 | A | | 5/1995 | Bastioli et al. | 524/47 |
| 5,610,214 | A | | 3/1997 | Olson | 524/311 |
| 5,635,194 | A | | 6/1997 | Dorn et al. | 424/405 |
| 5,679,364 | A | | 10/1997 | Levy | |
| 5,720,967 | A | | 2/1998 | Hall-Hibbitts et al. | 424/405 |
| 5,785,976 | A | | 7/1998 | Westesen et al. | 424/400 |
| 5,897,877 | A | | 4/1999 | Birrenbach et al. | |
| 5,858,384 | A | | 7/1999 | Levy | 424/406 |

FOREIGN PATENT DOCUMENTS

| | | | | |
|---|---|---|---|---|
| EP | 588707 | | * | 3/1994 |
| EP | 0 624 366 | A1 | | 11/1994 |
| EP | 0631 781 | A1 | | 1/1995 |
| EP | 0 647 448 | A1 | | 4/1995 |
| EP | 0 823 255 | A1 | | 2/1998 |
| GB | 2077103 | | * | 12/1981 |
| JP | 05271014 | | | 10/1993 |
| WO | WO 90/04386 | | | 5/1990 |
| WO | WO 92/20229 | | | 11/1992 |
| WO | WO 93/01804 | | | 2/1993 |

OTHER PUBLICATIONS

Shtilman et al. "Phytoactive Polymers: Hydrolysis and Bioactivity", Proceed. Intern. Symp. Control. Rel. Bioact. Mater., 23, 1996, pp. 33–34.

Bettini et al. "Osmotic Matrix for Controlled Drug Delivery" Proceed. Intern. Symp. Control. Rel. Bioact. Mater., 23, 1996, pp. 55–56.

Peppas et al. "Oral Delivery Devices From Freeze/Thawed Poly(Vinyl Alcohol) Hydrogels", Proceed. Intern. Symp. Control. Rel. Bioact. Mater., 23, 1996, pp. 145–148.

Peppas et al. "Mucoadhesive Poly(Vinyl Alcohol Films Produced By Freezing/Thawing Processes for the Release of Small Molecular Weight Solutes and for Wound Healing Systems" Proceed. Intern. Symp. Control. Rel. Bioact. Mater., 23, 1996, pp. 33–34.

Chi et al. "Protein Release From Microspheres of Star–Shaped Per–Plan Block Copolymers", Proceed. Intern. Symp. Control. Rel. Bioact. Mater., 23, 1996, pp. 349–350.

Akamatsu et al. "Development of Sustained Drug Delivery System Using Poly (vinyl alcohol) Hydrogen", Proceed. Intern. Symp. Control. Rel. Bioact. Mater., 23, 1996, pp. 793–794.

Aso et al. "Determination of the Diffusion Coefficient of Poly(L–Glutamic Acid) by Pulsed–Field–Gradient Spin–Echo NMR and its Release Rate From Poly(Vinyl Alcohol) Hydrogel", Proceed. Intern. Symp. Control. Rel. Bioact. Mater., 23, 1996, pp. 723–724.

Lee et al. "Enhanced Bioavailability of Ipriflavone With Buoyant Hydrophilic Matrices Systems", Proceed. Intern. Symp. Control. Rel. Bioact Mater., 23, 1996, pp. 803–804.

Takada et al. "Novel Microencapsulation Technique for Controlled Release of a Water–Soluble Non–Basic Drug", Proceed. Intern. Symp. Control. Rel. Bioact. Mater., 23, 1996, pp. 339–340.

Chun et al. "The Effect of Polymer Blending or Coating on the Preparation of Alginate Microspheres Containing Hydrophilic β–Lactam Antibiotic", Proceed. Intern. Symp. Control. Rel. Bioact. Mater., 23, 1996, pp. 343–344.

* cited by examiner

CONTROLLED DELIVERY COMPOSITIONS AND PROCESSES FOR TREATING ORGANISMS IN A COLUMN OF WATER OR LAND

This application is a Division of Ser. No. 08/074,813, filed Jul. 3, 1996, now U.S. Pat. No. 6,001,382, which is a continuation in part application of U.S. patent application Ser. No. 08/434,313 filed, May 2, 1995, now U.S. Pat. No. 5,698,210, which is a continuation in part application of Ser. No. 08/409,301, filed Mar. 24, 1995, abandoned which is a continuation in part application of U.S. patent application Ser. No. 08/406,344 filed Mar. 17, 1995, abandoned all of which are incorporated herein by reference.

BACKGROUND OF THE INVENTION

1. Field of Invention

The present invention is directed to compositions and processes for controlled delivery of bioactive agents to a population of aquatic organisms located in any planar or volumetric segment of a column of water by ground or aerial application techniques. Organisms of special interest are disease-carrying or biting or non-biting nuisance insects, and parasitic animals or plants, especially weeds. Compositions for controlled delivery of bioactive agents to terrestrial organisms are also described.

2. Description of Related Art

Various methods have been devised for delivering biologically active materials to control pests and vegetation. For example, Yaffe et al., U.S. Pat. No. 3,274,052 describes a process and a composition in which molten droplets of a normally solid toxicant are sprayed on the surface of a granular carrier whereupon they adhere to and solidify on the surface of the carrier as an adherent coating. When employed for treating aquatic environments, the specific gravity of the granules, and the rate of release of the toxicant is adjusted during the manufacture to provide surface, intermediate or bottom contact, or penetration into mud to control the specific organisms involved. Neither methods nor compositions are described for adjusting the specific gravity.

Hedges et al., U.S. Pat. No. 3,917,814, describes a non-poisonous insecticidal composition consisting of diatomaceous earth having a sorptive silica gel adhered to the surface.

Jacobson et al., U.S. Pat. No. 5,180,585, describes an antimicrobial composition consisting of inorganic core particles coated with a metal or metal compound having antimicrobial properties.

Thies et al., U.S. Pat. No. 4,464,317, describes a process for encapsulating a pesticide with an inorganic silicate coating. The encapsulated materials according to the inventors are capable of fragmenting upon storage in water to provide controlled release of a pesticide such as a mosquito control agent. Non-encapsulated materials were shown to have about half the active life of the encapsulated materials.

Levy, U.S. Pat. Nos. 4,818,534; 4,983,389; 4,983,390; and 4,985,251, describe various insecticidal, herbicidal, terrestrial, and flowable insecticidal delivery compositions based on bioactive materials and superabsorbent polymers.

One of the problems encountered in delivering bioactive materials to aquatic environments is that the aquatic organism to be treated is not immediately susceptible to being contacted with the bioactive material because of its location in a column of water either at the surface, the bottom, or some intermediate region in between. Because of the specific gravity of the bioactive material, in many instances it cannot be targeted to precisely treat the organisms of interest in the water column. By way of example, bioactive materials that have a specific gravity greater than water will generally be ineffective for treating aquatic organisms at the surface of a column, and vice-versa. Aquatic organisms that persist at some intermediate level are also difficult to treat for the same reason.

The foregoing illustrates that various delivery systems have been devised for bioactive materials, and the need to have a controlled delivery system suitable for delivering these materials to aquatic organisms. Although there is some suggestion that by adjusting the specific gravity of a toxicant composition of matter, it would be suitable for delivering the toxicant to an aquatic environment either at the surface, the bottom or at some intermediate level, the means for adjusting the specific gravity have not been disclosed.

Accordingly, the present invention is directed to compositions and processes for treating a population of one or more aquatic organisms in a column of water in which the foregoing and other disadvantages are overcome.

The present invention is also directed to compositions and processes for pretreating a dry (preaquatic) habitat area before it has been flooded by rain or tides, and which is a breeding site for the target aquatic organism(s), i.e. a preflood area. Pretreating a flooded aquatic habitat area before the target aquatic organism(s) breed is also within the scope of the invention, as well as flooded habitats where the organisms exist.

The foregoing illustrates that various delivery systems have been devised for bioactive materials, and the need to have a controlled delivery system suitable for delivering these materials to one or more terrestrial organisms, i.e. non-aquatic organisms. Although there are some systems that are available to provide control of these organisms, it would be advantageous to provide additional compositions for addressing the problems caused by such organisms whether they are plant, insect, or other animal pests.

Accordingly, the present invention is directed to compositions and processes for treating one or more terrestrial organisms in which the foregoing and other disadvantages are overcome.

Specifically, the advantages sought to be obtained according to the present invention are to provide compositions of matter or processes for treating a population of one or more aquatic organisms in a column of water, or one or more terrestrial organisms. Throughout the specification it is intended that the terms "treat," "treating," or "treatment" are intended to mean such things as enhancing development of an organism, prolonging life of an organism, stopping or reversing the development of a condition in an organism, stopping the development of an organism, eliciting a response from an organism, protecting an organism or eradicating an organism.

SUMMARY OF INVENTION

These and other advantages are realized by the present invention which comprises compositions of matter and processes which substantially obviates one or more of the limitations and disadvantages of the related art.

Additional features and advantages of the invention will be set forth in the written description which follows, and in part will be apparent from this description, or may be learned by practice of the invention. The objectives and other advantages of the invention will be realized and attained by the compositions of matter and processes particularly pointed out in the written description and claims hereof.

To achieve these and other advantages, and in accordance with the purpose of the invention, as embodied and broadly described, the invention comprises compositions of matter for treating an aquatic column of water comprising a bioactive agent as a component for treating a population of one or more aquatic organisms, a carrier component, and a coating component for regulating the controlled release rate (i.e. fast, slow, pulsed or delayed), and release profile (i.e. zero-order, first-order, and square-root-of-time kinetics) of the bioactive agent in water. The compositions of matter of the invention can optionally be combined with a binder component to aid in agglomerating the compositions, or a variety of formulation ingredients to enhance the performance of the compositions.

Compositions of matter are also described for treating a population of one or more aquatic organisms in a column of water comprising a bioactive agent as a component for treating a population of one or more aquatic organisms, and a joint-function carrier component that not only carries the bioactive material but also is a coating component for regulating the controlled release rate, and release profile of the bioactive agent in water. The compositions of matter of the invention can optionally be combined with a binder component to aid in agglomerating the compositions, or a variety of formulation ingredients to enhance the performance of the compositions.

Further in this regard, a composition of matter is provided comprising a complex for treating a population of one or more aquatic organisms in a column of water, the complex comprising at least one controlled delivery system wherein the controlled delivery system comprises at least one bioactive agent as a component for treating a population of one or more aquatic organisms, at least one carrier component, at least one coating component for regulating the controlled release rate, and release profile of the bioactive agent in water, with or without one or more binder components for agglomerating said composition into larger units such as granules, pellets, and briquets, or additional formulation ingredients.

In another complex, the controlled delivery system comprises at least one bioactive agent as a component for treating a population of aquatic organisms, at least one joint-function carrier component that is also a coating component for regulating the controlled release rate, and release profile of the bioactive agent in water, with or without one or more binder components for agglomerating said composition into larger units such as granules, pellets, and briquets, or additional formulation ingredients.

In yet another complex, the controlled delivery system comprises at least one bioactive agent as a component for treating a population of one or more aquatic organisms, at least one joint-function carrier component that is also a coating component for regulating the controlled release rate, and release profile of the bioactive agent in water, at least one additional component such as an additional coating component to further regulate or modify the controlled release rate, and release profile of the bioactive agent in water, with or without one or more binder components for agglomerating said composition into larger units such as granules, pellets, and briquets, or additional formulation ingredients.

The components are selected to sink or float so that each complex or composition will permeate, and remain in any planar or volumetric segment of a water column for a period of time sufficient to effectively treat a population of one or more aquatic organisms.

A method is also provided in which the foregoing compositions are delivered to the column of water in order to time-release the bioactive agent(s) in the water so as to make it available to treat the aquatic organisms.

The invention also comprises compositions of matter for treating one or more terrestrial organisms comprising a bioactive agent as a component for treating a population of one or more terrestrial organisms, an optional carrier component, and a coating component for regulating the controlled release rate, and release profile of the bioactive agent. These compositions of matter of the invention can optionally be combined with a binder component to aid in agglomerating the compositions, or a variety of formulation ingredients to enhance the performance of the compositions.

Compositions of matter are also described for treating a population of one or more terrestrial organisms comprising a bioactive agent as a component for treating a terrestrial organism, and a joint-function carrier component that not only carries the bioactive material but also is a coating component for regulating the controlled release rate, and release profile of the bioactive agent. The compositions of matter of the invention can optionally be combined with a binder component to aid in agglomerating the compositions, or a variety of formulation ingredients to enhance the performance of the compositions.

Further in this regard, a composition of matter is provided comprising a complex for treating a population of one or more terrestrial organisms, the complex comprising at least one controlled delivery system wherein the controlled delivery system comprises at least one bioactive agent as a component for treating a terrestrial organism, at least one optional carrier component, at least one coating component for regulating the controlled release rate, and release profile of the bioactive agent, with or without one or more binder component(s) for agglomerating said composition into larger units such as granules, pellets, and briquets, or additional formulation ingredients.

In another complex, the controlled delivery system comprises at least one bioactive agent as a component for treating a population of one or more terrestrial organisms, at least one joint-function carrier component that is also a coating component for regulating the controlled release rate, and release profile of the bioactive agent, with or without one or more binder components for agglomerating said composition into larger units such as granules, pellets, and briquets, or additional formulation ingredients.

In yet another complex, the controlled delivery system comprises at least one bioactive agent as a component for treating a population of one or more terrestrial organisms, at least one joint-function carrier component that is also a coating component for regulating the controlled release rate, and release profile of the bioactive agent, at least one additional component such as an additional coating component to further regulate or modify the controlled release rate, and release profile of the bioactive agent, with or without one or more binder components for agglomerating said composition into larger units such as granules, pellets, and briquets, or additional formulation ingredients.

A method is also provided in which the foregoing compositions are delivered to a terrestrial environment in order to time-release the bioactive agent(s) so as to make it available to treat the terrestrial organisms. The terrestrial environment is one that is a habitat or potential habitat for the terrestrial organisms.

It is understood that both the foregoing general description and the following detailed description are exemplary, and explanatory, and further, the following description is intended to provide a more detailed explanation of the invention as claimed.

DETAILED DESCRIPTION

Figure 2:
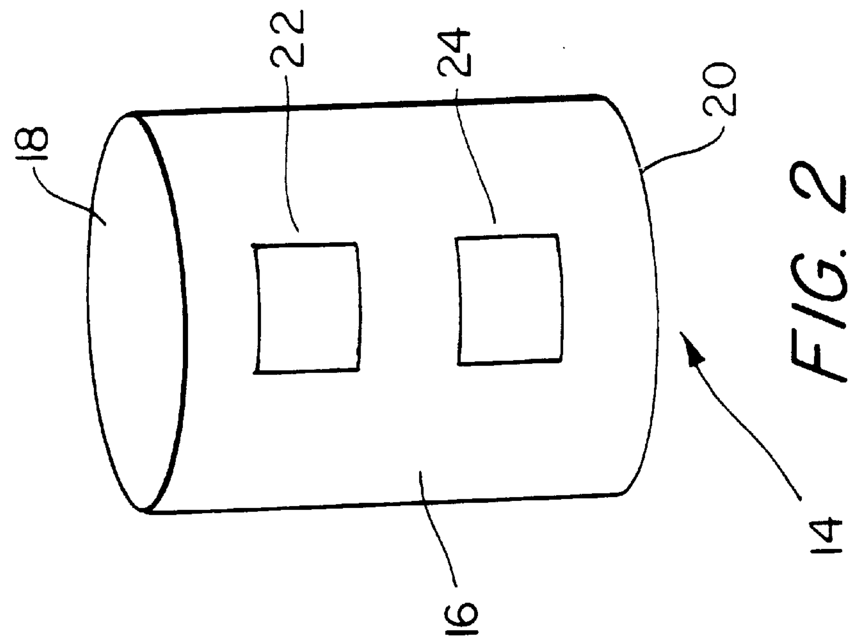
FIG. 2 is a perspective view of a dispensing container having apertures for dispensing the composition of the present invention to an aquatic or terrestrial habitat.
Figure 1:
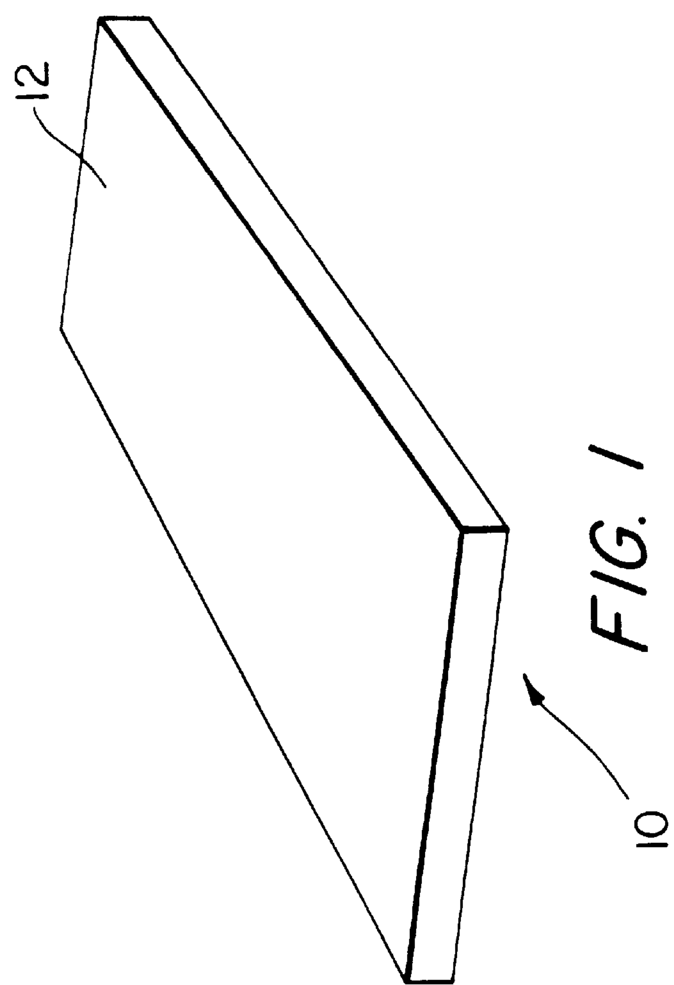
FIG. 1 is a perspective view of a porous, or degradable container, such as a water soluble polyvinyl alcohol pouch or film containing the composition of the present invention.

The effectiveness of bioactive materials, especially on aquatic organisms, is generally dependent on delivery of the material to the specific organisms that are targeted for treatment, i.e., effectiveness is dependent on the bioavailability of the material which can be problematic in aqueous environments. For example, some bioactive materials when delivered to an aqueous environment will not remain in the region of interest, where the aquatic organisms are located, for a length of time sufficient to provide complete treatment of the organism. This is generally remedied by several successive treatments which is costly in terms of the labor and machinery expenses incurred in multiple applications.

An example would be the use of a bioactive material having a specific gravity greater than one, used for the treatment of aquatic organisms that persisted at the surface of a body of water.

Similar problems would also occur where the bioactive material has a specific gravity less than one, and the aquatic organisms have a habitat beneath the surface of, or at the bottom of a body of water. In this case, the bioactive material could be injected by means of a tube or other device beneath the surface of the water, but since it has a specific gravity less than one, it would not persist in the region where it is delivered, and would also require multiple applications in order to be effective.

In order to overcome these difficulties, compositions and processes have been provided for treating a column of water where compositions can be specifically formulated to persist either at the top or the bottom of the column or at any planar or volumetric segment in between the top and the bottom.

One composition of matter of the present invention is based on at least one bioactive agent for treating a population of one or more aquatic organisms, at least one carrier component, and at least one coating component for regulating the controlled release rate, and release profile of the bioactive agent in water, with or without one or more binder components for agglomerating said composition into larger units such as granules, pellets, and briquets, or additional formulation ingredients.

A second composition of matter is based on at least one bioactive agent for treating a population of one or more aquatic organisms, at least one joint-function carrier component that is also a coating component for regulating the controlled release rate, and release profile of the bioactive agent in water, with or without one or more binder components for agglomerating said composition into larger units such as granules, pellets, and briquets, or additional formulation ingredients.

A third composition of matter is based on at least one bioactive agent for treating a population of one or more aquatic organisms, at least one joint-function carrier component that is also a coating component for regulating the controlled release rate, and release profile in water, and at least one additional component such as an additional coating component to further regulate or modify the controlled release rate, and release profile of the bioactive agent in water, with or without one or more binder components for agglomerating said composition into larger units such as granules, pellets, and briquets, or additional formulation ingredients.

In another embodiment, the invention relates both to a composition and process for treating a population of one or more terrestrial organisms. This comprises delivering to a terrestrial environment, a composition of matter comprising a complex for treating a population of one or more terrestrial organisms, the complex comprising at least one controlled delivery system wherein the controlled delivery system comprises at least one optional carrier component, at least one bioactive agent as a component selected for treating a population of one or more terrestrial organisms, and at least one high molecular weight organic plasticizer coating component for regulating the controlled release rate and release profile of the bioactive agent. The components are selected so the complex will remain in an application site for a period of time sufficient to effectively treat a population of one or more terrestrial organisms.

The various components are selected to sink or float so that each complex or composition will permeate, and remain in any planar or volumetric segment of a water column for a period of time sufficient to effectively treat a population of one or more aquatic organisms.

The aforementioned compositions of matter of the present invention can be placed in one or more differentially water soluble, flexible or rigid, porous, or degradable or biodegradable packets, pouches, capsules, canisters, extrusions, coatings, and the like, of polyvinyl alcohol, polyethylene oxide, and hydroxypropyl methyl cellulose films of various thicknesses (e.g., 1–3 mil) to further modify the coating regulated controlled release rate, and release profile of the bioactive agent(s) formulated in the powdered, granulated or agglomerated compositions.

Furthermore, the controlled release rate, and release profile of one or more bioactive agents from all compositions of matter of the present invention can be optionally modified by placing said compositions (i.e., liquid, powdered, or granular or agglomerated) into various shaped (e.g., spherical, cylindrical, etc.) disposable or reusable, biodegradable, porous, or degradable or nondegradable, dispensers (e.g., plastic or metal) such as water soluble polyvinyl alcohol pouch 10 having a continuous outer wall 12 that envelops the composition of the invention therein (not illustrated) or metal container 14 having outer wall 16 and bottom wall 18 and 20, with one or more orifices (e.g., holes, slots, etc.) 22 and 24 through which the bioactive agent formulation therein (not illustrated) will be delivered.

Dispensing devices can be of various densities for use in aqueous environments, and can be anchored in various surface, and/or subsurface locations of an aquatic habitat or can be freely dispensed to float, and/or sink at will. These optional dispensing devices can also be utilized in pretreatment or dry aquatic habitats that are scheduled to become aquatic e.g. by the advent of rain, and/or tides.

The carrier comprises a material that will float or sink, and is based on either inorganic or organic compounds that are hydrophobic or hydrophilic. Carriers can be any natural or synthetic material of any size, shape or texture and can be particulate such as powders granules, pellets, briquets or agglomerated or continuous in the form of extrusions, films, sheets or laminates.

Carriers can be porous or non-porous, rigid, semi-rigid flexible or elastic. Non-limiting examples of carriers include special interest materials such as silica (including sand and diatomaceous earth), cellulose fibers such as PRE-CO-FLOC® which is derived from purified virgin wood pulp, which is fully bleached in a sulfite pulp process having an average fiber length of from about 50 to about 90 microns, and a thickness of from about 7 to 30 microns, metal oxides, clays, paper, infusorial earth, slag, or lava, all of which may be finely ground or have a small particle size, but can be agglomerated into larger components with the addition of a binder component. Hydrophilic materials that have been surface treated to be hydrophobic, e.g., by a silicone coating are also suitable. Other carriers can include films sheets, or extrusions of polyvinyl alcohol, polyethylene oxide, and hydroxy propyl methyl cellulose, MONO-SOL® LXP-1832 which is a FDA approved hydroxypropyl methyl cellulose (MHPC) and is edible, MONO-SOL® PXPN-1257 MHPC, and the MONO-SOL® 6000, 7000 and 8000 series which are polyvinyl alcohol polymer or copolymer films, other polymer sheets, extrusions or films noted herein, thermolytically processed hydrophobic "pin chips" (waste wood, or saw dust) (Sea Sweep®), cetyl alcohol, stearyl alcohol, vermiculite, ground cork, corn cobs, bagasse from sugar cane or grapes and the like, seed, seed hulls from any cereal crop, such as rice, rice hulls, oats, oat hulls, wheat, wheat hulls, barley, barley hulls and the like, paper, and especially dust free paper granules such as BIODAC®, manufactured from recycled, cellulosic based paper waste and containing from about 47 to about 53 wt. % paper fiber, from about 28 to about 34 wt. % clay, and especially paper grade clays or mixtures thereof, including Kaolin, about 14 to about 20 wt. % calcium carbonate or art known equivalents thereof and mixtures thereof, and from about 0.01 to about 0.9 wt. % of an inorganic pigment such as titanium dioxide, or the art known equivalents thereof, and mixtures thereof. Other materials that may be employed as carriers include carbon materials such as charcoal, petroleum coke, coke from coal, CVD carbon, carbon black, lamp black, activated carbon, and graphite, rubber, gypsum, cement, concrete, asphalt, wood, fiber glass, glass, metals, metal alloys, clothing fabrics, plaster of Paris, mineral aggregate, leather, natural and synthetic fibers, liposomes, lipospheres, food proteins, such as zein and its equivalents, polymeric materials, such as olefinic polymer materials, e.g., homopolymers, and/or copolymers of polyethylene or polypropylene, fluorinated polymers such as polytetrafluoroethylene, or polyvinylidene fluoride, or chlorinated polymers such as polyvinyl chloride homopolymers and copolymers, acrylate polymers such as acrylic acid and alkyl acrylic acids or esters or amides including the homopolymers and copolymers thereof, and the like. Polysaccharides can also be employed as carriers including starches and modified starches, especially as both are described herein, carrageenan, algin, which is intended to include alginates as well, xanthates, and agar.

The carriers take any shape or form, including agglomerates, granules, pellets, briquets, fibers, fabrics, continuous sheets, discontinuous sheets, films, extruded rods, tubes, whether circular or multi-walled such as triangular, square, and the like. The carriers therefore present any surface for coating whether a continuous or a discontinuous surface. Granules, pellets, or briquets comprise especially suitable carrier shapes and sizes although other shapes find use such as powders and similar particulate configurations. The carriers can be combined to alter or enhance the performance characteristics of a composition, two, three or four carriers being especially suitable in this regard.

The especially preferred materials in this regard can comprise silicas and silicates.

Precipitated silicas employed in this regard are produced from solutions of water glass into which sulfuric acid is introduced under fixed conditions. They are formed in the aqueous phase, and depending on the conditions of precipitation, it is possible to produce products with smaller or somewhat larger primary particles, which then basically determine particle size and specific surface area. The precipitates obtained are then washed and dried by methods known in the art.

Silicates are also manufactured by a precipitation method, however, the acids which are necessary for precipitation are replaced partially or completely by solutions of metallic salts such as aluminum sulfate, and the like. The precipitation parameters can also be adjusted to suit the various raw materials.

The silicas obtained in this way can be dried by a spray drying technique to obtain particles that are substantially spherical, have a size anywhere from about 50 to about 150 μm, and have excellent flow properties.

Spray dried precipitated silicas may also be ground so that the densities will vary anywhere from about 80 g/l to about 270 g/l, and the particle size anywhere from about 4 μm to 100 μm.

Precipitated silicas and silicates can also be dried by standard drying processes, for example in turbo-driers or rotating driers. Silicas and silicates dried in this conventional way must always be subsequently ground. The average particle size and the tapped density also depend on the degree of grinding. The tapped density in this regard can be from about 80 g/l to about 240 g/l, and the particle size from about 4 μm to about 15 μm.

Silicas can also be produced by means of a high temperature flame hydrolysis during which silicon tetrachloride is hydrolyzed in an oxyhydrogen flame, which is sometimes referred to as pyrogenic silica. The tapped density of these silicas is somewhere around 50 g/l. Both the precipitated silicas and the pyrogenic silicas can be after-treated in a secondary stage in order to change the naturally hydrophilic surface to a hydrophobic surface e.g. by a suitable chlorosilane to react with a silanol group on the surface of the silica.

The silicas and silicates are further described in *Technical Bulletin Pigments, Synthetic Silicas For Plant Protection and Pest Control,* No. 1 Degussa, Pig. 27-6-2-79OME, 5th Ed., Date of Issue: Jul. 19, 1990, CAB-0-SIL® FUMED SILICAS, TD-117 7M/11/92, Copyright 1990 Cabot Corporation, and Bergna, *The Colloid Chemistry of Silica,* ACS, 1994 all of which are incorporated herein by reference.

Silicas that are especially suitable, include both the hydrophilic and the hydrophobic silicas which have been treated with a chlorosilane, and generally have a surface area of from about 50 to 450 $m^2/g$, an average agglomerate size of from about 3.5 to about 100 μm, or an average primary particle size of from about 12 to 30 nm, a tapped density of from about 50 to 240 g/l, a pH of from about 3.6 to about 9, and a DBP adsorption of about 160 to 335 g/100 g.

The silicates that may be employed in this regard comprise those that have a surface area from about 30 to about 40 $m^2/g$, an average agglomerate size of from about 4 to about 6 μm, a tapped density of from about 285 to 315 g/l, a pH of from about 9.5 to about 10.5, and a DBP adsorption of from about 150 to about 170 g/100 g.

The other inorganic carriers and some of the polymeric organic carriers noted in this regard will also have substantially the same surface area and particle size, although the density will vary depending upon the material employed. Larger surface areas and particle sizes can also be utilized. Extruded films that are water-soluble can also be effective carriers in certain formulations. Other carriers that may be employed are described by Stilman, *Immobilization On Polymers,* 1983 which is incorporated herein by reference.

The various bioactive agents that are employed in the compositions of the present invention to treat populations of adult or immature (e.g., egg, larvae, pupae, nymphs) organisms comprise technical or formulated (technical plus inerts) pesticides, insecticides, toxicants, monomolecular surface films, petroleum oils, insect growth regulators, plant growth regulators, animal growth regulators, microbial control agents, pharmaceuticals, medicaments, antibiotics, pathogens, bioactive control agents, parasites, pharmaceuticals or medicaments, bactericides, and viricides, fungicides, algaecides, herbicides, nematicides, amoebicides, acaricides, miticides, predicides, schistisomicides, molluscicides, larvicides, pupicides, ovicides, adulticides, nymphicides, attractants, repellents, growth stimulants, feeding stimulants, nutrients, hormones, chemosterilants, or pheromones, fragrances, flavorants, food additives and combinations thereof, such as the two, three or four component combinations. Two or more bioactive agents can be combined in the same composition to achieve multi functional performance from a single application.

Insecticidal bioactive materials include *Bacillus thuringiensis,* and especially subspecies *kurstaki* and *israelensis, Bacillus sphaericus, Bacillus popilliae, Seriatia marcescens,* and *Lagenidium giganteum,* which are sometimes referred to as bioactive agents employed for the control of insects. Fungal larvicides may also be employed such as *Lagenidium giganteum* mycelium or *Lagenidium giganteum* oospores or mixtures thereof. Pyrethrin and pyrethroid larvicides can also be used. Fungal materials can also be effective against mosquito larvae. Insect growth regulators can be used such as (S)-methoprene, diflubenzuron, or pyriproxyfen. Aliphatic petroleum hydrocarbons may also be used as mosquito larvicides or non-petroleum hydrocarbon oils that form a monomolecular film on the water to be treated. Compositions and processes for control of various species of mosquitoes, and other pest dipterans in aquatic habitats are of particular interest. Bioactive agents of specific interest for use in these compositions include *Bacillus thuringiensis* var. *israelensis, Bacillus sphaericus, Lagenidiurn giganteum,* methoprene, diflubenzuron, pyriproxyfen, temephos, 2 mol ethoxylate of isostearyl alcohol, lecithins, and petroleum oils, and combinations thereof, such as the two, three or four component combinations. Other insecticides may also be employed including products such as malathion, resmethrin, dichlorvos, bendiocarb, fenitrothion or chlorpyrifos. Insecticides such as pyrethrin and pyrethroid can be effective as larvicides for mosquitoes.

Various herbicides that may be employed, especially effective aquatic herbicides include Amitrole®, ammonium sulfamate, Bromacil®, copper salts, dalapon, Dichlorbenil®, Diquat®, Diuron®, Endothall®, Fenac®, Picloram®, Prometon®, Silvex®, Simazine®, trichloroacetic acid, 2,4-D, 2,4,5-T, Velpar®, TSMA, dicamba, endothall, silvex, prometon, chlorate, sodium metaborate, monuron, and various combinations thereof, such as the two, three or four component combinations. Other insecticides, herbicides or fungicides that may be employed are set forth by Page & Thomson *The Quick Guide,* Thomson publications 1987, Thomson, *Agricultural Chemicals,* Book I, Insecticides; Book II, Herbicides; Book III, Fumigants, Growth Regulators, Repellants, 1985–87 revisions, all of which are incorporated herein by reference.

Control of floating and submersed aquatic weeds is also of special interest. Bioactive agents included in the compositions and processes for these applications include acrolein, aromatic solvents (xylene), copper sulfate and other water soluble copper salts or compounds, dalapon, dichlorbenil, 2,4-D, diquat, endothall, glyphosate, simazine, and fluridone, and combinations thereof, such as the two, three or four component combinations.

The aquatic organisms that are of special interest and which can be treated by the compositions of the present invention, and in accord with the methods of the present invention include disease carrying or biting or non-biting insects (e.g., mosquitoes, sand flies, black flies, midges), or other animals (e.g., fish, barnacles, snails) or aquatic and wetland plants, and especially parasitic animals (e.g., nematodes, mollusks, protozoans, and bacteria) or floating or submersed nuisance weeds e.g., algae, duckweed, hydrilla, water hyacinth, chara, watermilfoil, cattail bass weed, burreed, coontail, and the various pondweeds including bushy, curly-leaf, flat stem, floating-leaf, horned, and sago; water star grass, arrowhead, bladderwort, bulrush, hornwort, creeping water primrose, pickerelweed, spatterdock, cow lily, yellow water lily, waterweed, water chestnut, water smart weed, white water lily, naiad, watershield, elodea, hydrollia, alligatorweed, cattails, giant cutgrass, guineagrass, knotgrass, maidencane, paragrass, phragmites, spatterdock, and torpedograss.

It should be noted that any bioactive agent, and combinations thereof, such as the two, three or four component combinations, designed for promoting, enhancing (e.g., nutrients, flavorants, medicaments) or terminating (e.g., pesticides, or herbicides) the life of aquatic or terrestrial organisms can be utilized in the compositions of matter, depending on the desired end result. Specific controlled release compositions will be designed to deliver the desired bioactive agent(s) in the targeted portion(s) of the water column of an aquatic habitat or to a specific targeted area of a land mass.

These bioactive materials, and organisms are further described by Levy in U.S. Pat. No. 4,818,534, columns 12–14; U.S. Pat. No. 4,983,389, columns 11–13; U.S. Pat. No. 4,985,251, columns 4, 10, and 12–14; all the foregoing being incorporated herein by reference.

The coatings that may be employed according to the present invention are selected so as to act as materials that will regulate the controlled release rate and release profile of bioactive agents over a period of time in an aqueous or non-aqueous medium, and accordingly have to be water soluble or partially water soluble and biodegradable, or insoluble in water, and biodegradable or erodible, and/or film-forming on contact with water. Coatings may also protect bioactive agents from photodegradation or biodegradation. The coatings have a specific gravity equal to or greater than one or less than one, and are liquids or solids, and generally consists of either fatty alcohols or acids, or fatty alcohol esters of citric, glycolic, trimelletic or phthalic acid, or any mono, di- or tricarboxylic acid having from one to about 18 carbon atoms, whether saturated or unsaturated, aliphatic or cyclic, and which are well known in the art. The fatty alcohols in this regard comprise those alcohols having from about 5 to about 18 carbon atoms, and include the saturated as well as unsaturated aliphatic fatty alcohols. The aliphatic acids or alcohols include the straight chain and branched chain isomers.

The coatings having a specific gravity less than one may comprise n-butyryl-tri-n-hexyl citrate, monostearyl citrate, stearyl alcohol, cetyl alcohol, myristyl alcohol, octadecanoic acid, glyceryl stearate, or waxes whereas the coatings having a specific gravity greater than one may comprise, triethyl, acetyltriethyl citrate, tri-n-butyl citrate, acetyltri-n-butyrl citrate, acetyltri-n-hexyl citrate, tri-n-hexyltrimellitate, dicyclohexyl phthalate, diethyl phthalate, butyl phthalyl butyl glycolate, dimethyl isophthalate, or water-soluble films of polyvinyl alcohol, polyethylene oxide, methyl cellulose, and hydroxypropyl methyl cellulose, and combinations thereof, such as the two, three or four component combinations. It should be noted that water-soluble films can act in a coating/carrier capacity in certain compositions of matter. Two or more coatings can be combined to modify or enhance the controlled release rate or release profile of one or more bioactive agents in a composition.

One aspect of the invention comprises applying the coating with the bioactive material to the carrier and/or any continuous or discontinuous surface such as walls, foundations, screening, fibers, fabrics, clothing and the like. Thus in terrestrial applications, the composition of the invention comprises at a minimum, the coating material and the bioactive agent that can be appplied to any substrtate, including the carrier, where the carrier comprises an optional component.

Especially suitable coatings comprise high molecular weight organic plasticizer coatings and include by way of example the following materials:

Acetates
Glycerol diacetate
Glycerol monoacetate
Glycerol triacetate
Cumylphenyl Acetate
triethylene glycol diacetate
Adipic Acid Derivatives
Dibutoxyethoxyethyl adipate
Dicapryl adipate
Di(2-ethylhexyl) adipate
Di(n-heptyl,n-nonyl)adipate
Diisobutyl adipate
Diisodecyl adipate
Diisononyl adipate
n-Octyl, n-decyl adipate
Dioctyl adipate
Di(tridecyl)adipate
Alkyl alkylether diester adipate
Dibutoxyethoxyethyl adipate
Dibutoxyethyl adipate
Dimethyl adipate
n-Octyl,n-decyl adipate
Polyester adipate
Poly(propylene glycol adipate)diol cocoate
Poly(neopentyl glycol adipate)diol
Poly(diethylene glycol adipate)diol
Azelaic Acid Derivatives
Dibutyl azelate
Di-(2-ethylhexyl) azelate
Diisodecyl azelate
Diisooctyl azelate
Dimethyl azelate
Di-n-hexyl azelate
Dibenzyl azelate
Dibutoxyethyl azelate
Diisobutyl azelate
Dioctyl azelate
Benzoic Acid Derivatives
Benzyl Benzoate
Diethylene gycol dibenzoate
Dipropylene glycol dibenzoate
Glycerol dibenzoate
Polyethylene glycol 200 dibenzoate
Propylene glycol dibenzoate
Tripropylene glycol dibenzoate
Tetrapropylene glycol dibenzoate
Octadecy benzoate
Glucose benzoate
2,2,4,-trimethyl-1,3-propanediol dibenzoate
Pentaerythritol tetrabenzoate
1,6-Cyclohexane dimethanol dibenzoate
Caprylic/Caproic Acid Derivatives
N,N-Dimethyl caprylamide capramide
Propylene glycol dicarprylate/caprate
Tetraethylene glycol dicaprylate/caprate
Triethylene glycol caprylate/caprate
Trimethylolethane tri caprylate/caprate
Trimethylopropane tri caprylate/caprate
Pentaerythritol tetra caprylate/caprate
Citric Acid Derivatives
Acetyltri-n-butyl citrate
Acetyl triethyl citrate
Acetyltri-n-(octyl/decyl) citrate
Acetyl-n-trihexyl citrate
n-Butyltri-n-hexyl citrate
Stearyl Citrate
Monostearyl citrate
Tri-n-butyl citrate
Triethyl citrate
Triethyl citrate polyethylene glycol
Trimethyl citrate
Coco Acid Derivatives
Tetraethylene glycol dicocoate
Dimer Acid Derivatives
Bis-(2-hydroxyethyl) dimerates
Epoxy Derivatives
Epoxidized linseed oil
Epoxidized soybean oil
2-Ethylhexyl epoxytallate
Epoxidized octyl tallate
Epoxidized glycol dioleate
Fumaric Acid Derivatives
Dibutyl fumarate
Glutarates
Long chain alkyl alkylether diester
Dialkyl diether glutarate
Dibutoxyethoxyethyl glutarate
Dibutoxyethyl glutarate
Diisodecyl glutarate
Polyester glutarate
Glycolic Acid Derivatives
n-butyl-phthalyl-n-butyl glycolate
Heptanoic Acid Derivatives
Tetraethylene glycol diheptanoate
Triethylene glycol diheptanoate
Tetraethylene glycol diheptanoate
Trimethylopropane triheptanoate
Isobutyrate Derivatives
2,2,4-Trimethyl-1,3-pentahedial, diisobutyrate
Isophthalic Acid Derivatives
Dimnethyl isophthalate Diphenyl isophthalate
Lauric Acid Derivatives
Dioctyl dodecanedjoate
Diisooctyl dodecanedjoate
Isopropyl laurate
Methyl laurate
Polyethylene glycol 400 dilaurate
Polyethylene glycol 200 monolaurate
Polyethylene glycol 400 monolaurate
Polyethylene glycol 600 monolaurate
Polyoxyethylene laurate
Polyoxyethylene laurate, self emulsifying
Linoleic Acid Derivatives
Methyl linoleate, 50%
Maleic Acid Derivatives
Di(2-ethylhexyl) maleate
Di-n-butyl maleate
Mellitic acid Derivatives
Tricapryl trimellitate
tri-n-hexyl-trimellitate
Triisodecyl trimellitate
Triisononyl trimellitate
Tri-(n-octyl, n-decyl) trimellitate
Trioctyl trimellitate
Myristic Acid Derivatives
Ispropyl myristate
Octanoic Acid Dyrivatives
Propylene glycol di-2-ethylhexonoate
Trimethylolpropane trioleate
Pentaerythritol tetraoleate
Polyethylene glycol 400 di-2-ethylhexoate
Tetrathylene glycol di-2-ethylhexoate
Triethylene glycol di-2-ethylhexoate
Oleic Acid Derivatives
Butyl oleate
Glycerol monooleate
Glycerol trioleate
Methyl oleate
n-Propyl oleate
Tetrahydrofurfuryl oleate
Alkyl oleate
Butoxyethyl oleate
Glycerol oleate
Polyethylene glycol 400 dioleate
N,N-Dimethyl oleamide
Polyethylene glycol 200 monooleate
Polyethylene glycol 600 monooleate
Trimethylolpropane trioleate
Pentaerythritol tetraoleate
Palmitic Acid Derivatives
Isopropyl palmitate
Methyl palmitate
Paraffin Derivatives
Chloroparaffin, 41% Cl
Chloroparaffin, 50% Cl
Chloroparaffin, 60% Cl
Chloroparaffin, 70% Cl
Pelargonic Acid Derivatives
Triethylene glycol dipeargonate
Phosphoric Acid Derivatives
2-Ethylhexyl diphenyl phosphate
Isodecyl diphenyl phosphate
t-Butylphenyl diphenyl phosphate
Tri-butoxyethyl phosphate
Tributyl phosphate
Tricresyl phosphate
Triphenyl phosphate
Phthalic Acid Derivatives
Alkyl($C_7$/$C_9$)benzyl phthalate
Butyl benzyl phthalate
Butyl octyl phthalate
Di-n-butyl phthalate
Dibutoxyethoxyethyl phthalate
Dicapryl phthalate
Dicyclohexyl phthlate
Di-(2-ethylhexyl) phthalate
Diethyl phthalate
Diheptyl, nonyl, undecyl phthalate
Dihexyl phthalate
Diisobutyl phthalate
Diisodecyl phthalate
Diisoheptyl phthalate
Diisononyl phthalate
Diisooctyl phthalate
Dimethyl phthalate
Dinonyl phthalate
Dinonyl, undecyl phthalate
Ditridecyl phthalate
Diundecyl phthalate
Undecyl dodecyl phthalate
Ricinoleic Acid Derivatives
Butyl ricinoleate
Glyceryl tri-(acetyl) ricinoleate
Methyl acetyl ricinoleate
Methyl ricinoleate
n-Butyl acetyl ricinoleate
Propylene glycol ricinoleate
Sebacic Acid Derivatives
Dibutyl sebacate
Dibutoxyethoxyethyl sebacate
Dibutoxyethyl sebacate
Di-(2-ethylhexyl) sebacate
Dioctyl sebacate
Dimethyl sebacate
Polyester sebacate
Stearic Acid Derivatives
Ethylene glycol monostearate
2-Ethylhexyl stearate
Tridecyl stearate
Glycerol monostearate
Isopropyl isostearate
Methyl stearate
n-Butyl stearate
Isobutyl stearate
Propylene glycol monostearate
Stearic acid ester amide
Succinic Acid Derivative
Diethyl succinate
Sulfonic Acid Derivatives
N-n-Butylbenzenesulfonamide
N-Ethyl o,p-toluenesulfonamide
o,p-Toluenesulfonamide
Mineral oil/sulfonate blend
Mineral oil/sulfonate ester blend
Naphthenic oil/sulfonate ester blend
Tallates
Epoxidized tallate
Isooctyl tallate
Octyl tallate
Toluic Acid Drivatives
N-N-Diethyl m-toluamide
Flame-retardant Plasticizers
SANTICIZER® 2148 alkyl aryl phosphate-(liquid)
SANTICIZER® 148 alkyl aryl phosphate-(liquid)

SANTICIZER® 141 alkyl aryl phosphate-(liquid)
SANTICIZER® 143 modified triaryl phosphate-(liquid)
Alkylene Glycols and Esters
methoxy polyethylene glycol, poyethylene glycol and propylene glycol polymers and copolymers with one another, about 190 to about 19,000 M.W.

Miscellaneous

Hydrogenated Terphenyl HB-40®
Nipol® Liquid Nitrile Elastomers
JAYFLEX® 210 Plasticizer
(naphthenic hydrocarbon)
JAYFLEX® 215 Plasticizer
(aliphatic hydrocarbon)
STAN-FLUX™
Aromatic Process Oils
STAN-LUBE™
Paraffinic Process Oils
2-Hydroxyethyl ethylene Urea
Dibutoxyethoxyethyl formal
Polyol Esters made by reacting short to long chain carboxylic ($C_5$–$C_{18}$) acids with neopentyl polyols such as neopentyl glycol, trimethyloethane, trimethylopropane, and pentaerythritol
LEXOLUBE®—Isopropyl Esters where isopropyl alcohol is reacted with straight chain fatty acids ranging from lauric (C-12) to stearic (C-18) acid to produce an highly esterified product
Polyoxyethylene Esters made by reacting medium to long chain ($C_8$–$C_{18}$)carboxylic acids with tetraethylene glycol
LEXOLUBE®—Complex esters (the Z-series) ranging from a viscosity (40° C.) of 200 to 1000 centistokes based upon adipic acid backbone chemistry
LEXOLUBE® derived from the condensation of isobutanol with a triple pressed grade of stearic acid
LEXOLUBE® derived from the esterification of myristic acid (tetradecanoic acid) with isopropanol (2-propanol)
LEXOLUBE® Z-100 derived from the co-condensation of poly(propylene glycol adipate)diol with coconut fatty acid
LEXOLUBE® T-110 derived from the condensation of 2-ethylhexanol with a triple pressed grade of stearic acid
LEXOLUBE® 2J-237 derived from the condensation of tetraethylene (TEG) glycol with a whole cut grade of coconut fatty acid
LEXOLUBE® 2N-237 derived from the condensation of tetraethylene glycol (TEG) with a carboxylic acid blend consisting primarily of octanoic acid and decanoic acid
LEXOLUBE® 2N-237 derived from the condensation of tetraethylene glycol (TEG) with a carboxylic acid blend consisting primarily of octanoic acid and decanoic acid.

The range of molecular weights for the high molecular weight organic plasticizer coating component will range from the approximate molecular weight of the lowest molecular weight compound listed herein to approximately the highest molecular weight of the compounds listed above.

These high molecular weight organic plasticizer compounds also include epoxidized vegetable oils, naphthenic hydrocarbons and long chain aliphatic hydrocarbons or paraffin type oils as well as chlorinated paraffins all of which are well known in the art and noted above.

Ester coating compounds are especially preferred, particularly the esters listed herein.

The foregoing high molecular weight organic plasticizer compounds especially comprise organic esters based on the reaction of organic acids and organic alcohols or inorganic acids and organic alcohols where the inorganic acids comprise phosphorous acids and sulfur acids known in the art.

The organic acid esters are especially preferred, and particularly organic acids having from 1 to about 4 carboxyl groups, up to about 18 carbon atoms and can be saturated or unsaturated straight chain or cyclic structures including polyunsaturated compounds such as aromatic compounds and aliphatic or alicyclic compounds.

The preferred organic alcohols have from 1 to about 4 hydroxy groups, up to about 18 carbon atoms and can be saturated or unsaturated straight chain or cyclic structures including polyunsaturated compounds such as aromatic compounds and aliphatic or alicyclic compounds.

The coatings based on the high molecular weight organic plasticizers have a release profile controlled by solubility, hydrolysis, biodegradation, erosion, and/or other types of degradation of the esters (when employed) as well as other additives.

In addition to being applicable to treating organisms in columns of water and in surface or sub-surface areas of terrestrial habitats in the manner set forth herein, these compositions of matter comprising a controlled delivery system based on these high molecular weight organic plasticizers and other coating materials find use as seed coatings, medicament coatings, e.g., trans dermal patches or implants or admixtures with medicaments and the like.

In one application, in order to minimize allergic reactions of hooved animals to the application of various bioactive materials as defined herein, e.g. a repellant, the compositions find use in coating the hooves of hooved animals where the bioactive material vaporizes and moves upwards towards the animal, and/or remains in or on the ground. In some instances, where the bioactive material or combination of bioactive it materials include those that are not vaporizable, the application of the composition of matter to the feet of the animal will provide a way of applying the composition to the terrestrial environment of the animal and can find use for the treatment of marshy or swamp areas, e.g., for immature mosquitoes, as well as dry land areas where the animal moves about.

In addition, in those applications that do not involve treating a column of water, the compositions of the invention find use in coating fibers, fiber glass, walls, baseboards, building materials, (including wallboards, e.g. gypsum, press board, concrete blocks, cement walls and the like) to make the composition of the invention available for treating terrestrial organisms.

The coatings, bioactive agents and carriers may also be combined with water soluble or insoluble, hydrophilic or hydrophobic, biodegradable or erodible, cross-linked or non-crossed-linked, binder materials such as sulfonated polystyrene homopolymers, sulfonated styrene maleic anhydride polymers, sulfonated vinyl toluene maleic anhydride polymers, vinyl pyrrolidine polymers or copolymers, poly (isobutylene-co-disodium maleate) copolymers, acrylamide polymers or copolymers, acrylonitrile-starch graft polymers or copolymers, carboxymethyl cellulose polymers or copolymers, acrylate polymers or copolymers poly(vinyl alcohol) polymers or copolymers, poly(ethylene oxide) polymers or copolymers, acrylic acid or acrylic ester homopolymers or copolymers, modified food starch (CAPSULE® and N-LOCK®), natural or synthetic gums, poly(ethylene glycol), clays, gypsum, plaster of Paris, wax, paper, and especially paper as described herein including without limitation, BIODAC®, cellulose, latex, methyl vinyl ether maleic acid ester copolymers, and various starches and modified starches as described by Davidson *Book Of Water-Soluble Gums And Resins,* 1980, chapter 22, BP.22-1 to 22-79 which is incorporated herein by reference, and combinations thereof such as the two, three or four component combinations to agglomerate the controlled release compositions into larger units such as granules, pellets, briquets, or extrusions.

The foregoing polymers or copolymers which comprise superabsorbent polymers are especially useful in forming agglomerates of the compositions of the present invention. The various processes are known for forming these agglomerates some of which are described in *Ferro-Tech General Catalog,* Form 317, Aug. 1, 1983, revised 12-85 which is incorporated herein by reference, and is published by the Ferro-Tech® Corporation, 467 Eureka Road, Wyandotte, Mich. 48192, which is incorporated herein by reference.

The controlled release compositions may also be combined with other formulating materials or ingredients or components wherein such components are diluents, adjuvants, dyes, alcohols, acetone, ketones, oils, surfactants, water, emulsifiers, film-forming agents, compatibility agents, wetting agents, salt, natural or synthetic polymers, hydrocolloids, buoyancy modifiers, ultraviolet absorbers, photo-protecting agents, suspending agents, elastomers, penetrants, deflocculating agents, dispersing agents, stabilizing agents, antifoaming agents, sticking agents, solvents, co-solvents, catalysts, or synergists, and the like, and combinations thereof, such as the two, three or four component combinations.

Components of the present invention can be homogeneously or heterogeneously combined into the desired controlled delivery compositions or complexes for treating a population of aquatic organisms in an aquatic or preaquatic or terristrial environment by admixing the individual solid, and/or liquid formulation components in a concentration, and order to effectively impregnate or encapsulate the carrier (s) with the desired concentration of coating agent(s) and bioactive agent(s).

Admixing with one or more optional binders, and/or formulation materials can be utilized to agglomerate the composition(s) into larger units, and/or to achieve optimum controlled release performance. Formulation components can also be fabricated into solid controlled delivery compositions by coupling aqueous admixing procedures with solvent based admixing procedures.

To further modify the controlled delivery rate and release profile of compositions of matter of the present invention, liquid, powdered, granular, film or agglomerated compositions can be placed into flexible or rigid polyvinyl alcohols, polyethylene oxide, and/or hydroxypropyl methyl cellulose film containers (e.g., pouches, packets, capsules, extrusions) of varying water solubilities. In addition, compositions can be optionally placed into various shaped (e.g., spherical, cylindrical, etc.) dispensers (e.g., plastic, glass, metal, etc.) having a specific gravity greater than or less than one, with one or more orifices (e.g., holes, slots, etc.) in the wall(s) of the dispensing device to modify the controlled release rate and release profile of the bioactive agent from the compositions of matter through the orifice(s) into a water column. Pretreatment application of these dispensing devices is also within the scope of the present invention.

An example of a commercially available products that may be employed in this regard comprise DISSOLVO™-POUCH which is a polyvinyl alcohol film pouch. The various dimensionally stable solvable pouches are further describe by Miller in *Pesticides Formulations and Application System; 8th Vol., ASTM STP* 980, D. A. Hovde et al., EDS. American Society for Testing and Materials, Phil. 1988, which is incorporated herein by reference.

The compositions of the present invention can be formulated to time-release one or more bioactive agents from the carrier to treat a population of organisms in specific areas of a water column of an aquatic environment or in specific surface or subsurface areas of a terrestrial environment according to zero-order, first-order, or square-root-of-time kinetics. In general, depending on the type, concentration, and number of coatings utilized on a composition, and the formulation procedures utilized in fabricating the compositions, controlled delivery of one or more bioactive agents from the carrier can be fast, slow, delayed or pulsed. Controlled release formulations can be prepared wherein the materials for the preparation of such controlled release compositions are described by Wilkins, *Controlled Delivery Of Crop-Protection Agents,* 1990, Kydonieus, *Controlled Release Technologies: Methods, Theory And Applications,* Volumes 1 and 2, 1980; Barker *Controlled Release Of Biologically Active Agents,* 1987, Marrion, *The Chemistry And Physics Of Coatings,* 1994; Muller *Carriers For Controlled Drug Delivery And Targeting,* CRC press; Duncan and Seymour, *Controlled Release Technology* 1989; and Karsa and Stephenson, *Encapsulation And Controlled Release* 1993, all of which are incorporated herein by reference.

Controlled release solid compositions utilized in the present invention for treating a population of one or more aquatic organisms consist of about 0.001% to about 50% by weight (w/w) of at least one coating agent, about 0.0001% to about 50% (w/w) of at least one bioactive agent, and about 50% to about 99% (w/w) of at least one carrier; with or without about 0.0001% to about 75% (w/w) of one or more binders, and/or one or more formulating materials or about 0.1% to about 99.9% (w/w) of at least one joint-function carrier/coating agent, about 0.001% to about 90% (w/w) of at least one bioactive agent; with or without about 0.0001% to about 75% (w/w) of one or more binders, and/or one or more formulating materials.

Controlled release solid compositions utilized in the present invention for specifically treating a population of one or more species of mosquitoes in their aquatic stages, typically consist of about 1.0% to about 25% (w/w) of at least one coating agent, about 0.01% to about 30% (w/w) of at least one bioactive agent, and about 70% to about 95% (w/w) of at least one carrier; with or without about 0.01% to about 60% (w/w) of one or more binders, and/or formulating materials or about 50% to about 99% (w/w) of at least one joint-function carrier/coating, about 0.1% to about 30% (w/w) of at least one bioactive agent; with or without about 0.01% to about 60% (w/w) of one or more binders, and/or formulating materials. Solid compositions of the present invention can optionally be suspended in water or oil for application as a liquid spray.

In the embodiment of the present invention comprising complexes for treating a population of one or more aquatic organisms in a column of water, the complexes comprise at least one controlled delivery system, and especially from about one to about three controlled delivery systems. Each controlled delivery system in turn comprises at least one carrier, at least one bioactive agent as a component for treating a population of one or more aquatic organisms, and at least one coating component or at least one joint-function carrier/coating agent for regulating the controlled release rate and release profile of the bioactive agent in water with or without one or more binder components as an agglomeration aid or one or more additional formulation materials, which is intended to mean anywhere from one to about three of each of these components.

By properly selecting one or more of the various bioactive components, and/or other components, a composition of matter can be provided that will be effective to treat a population of one or more aquatic organisms or a plurality of aquatic organisms at either the surface, subsurface, the bottom or, the entire column of water.

Each one of these components is selected to sink or float so that the complex will permeate and remain in any planar or volumetric segment of a water column for a period of time sufficient to treat a population of one or more aquatic organisms.

It should be noted in this regard that even though silica has a specific gravity greater than one, a finely divided silica that has been surface treated with silicone, as noted herein, will float because of the hydrophobic properties imparted to it by the silicone coating. Accordingly, the hydrophobicity of the components in the composition of matter has to be taken into account when formulating the composition of the present invention by adjusting the type, and/or quantity of the hydrophobic component(s) employed.

Similarly, the density or the flotation properties of the other components of the compositions of matter of the invention have to be taken into account, as well as the quantity of such components when formulating the compositions of the invention so that it will be delivered to the appropriate planar or volumetric segment of the column of water that is to be treated according to the processes of the invention. When this formulation method is employed, a controlled delivery composition of matter can be prepared having a buoyancy selected to treat any part of a water column, or an entire water column.

Thus, a controlled delivery composition of matter can be prepared based on a carrier that sinks, and a bioactive material and coating that floats, each being employed in amounts that can be readily determined, so that the bioactive material will be taken to the bottom of a water column by the carrier, and upon exposure to water in the column, the coating will be released, and carry the bioactive material to the surface to treat any surface organisms or any organisms encountered in moving toward the surface. An example of a controlled delivery system like this comprises sand coated with the optimum concentration of cetyl alcohol in combination with a bioactive material that floats.

Similarly, a carrier can be selected that floats in combination with a coating that floats, and a bioactive material that sinks, where the types and quantities of each are experimentally determined so that the composition floats. Upon exposure to water, the coating will release the bioactive material which will move towards the bottom of the column, and treat any aquatic organisms that are at the bottom or encountered in moving toward the bottom of the column. An example of a controlled delivery composition of matter that will function in this way comprises silica that floats, i.e., hydrophobic finely divided silica coated with a silicone material, in combination with cetyl alcohol, and any known bioactive material that sinks.

Another controlled delivery composition of matter can be prepared based on a carrier and bioactive agent that sinks, and a coating that floats each being employed in amounts that can readily be determined so that the bioactive material will be taken to the bottom of a water column by the carrier, and upon exposure to the water the coating will be released, and initially carry the bioactive agent to the surface to treat any surface organisms encountered in moving toward the surface, and then after being maintained at the surface for some period of time, the bioactive agent will slowly move toward the bottom where it will be available to treat organisms on the downward movement through the water column, and at the bottom of the water column. An example of a controlled delivery system like this comprises sand coated with an optimum concentration of cetyl alcohol in combination with a bioactive agent that sinks.

Furthermore, compositions of matter of the invention comprising a joint-function carrier/coating agent, and bioactive agent, such as a sinking, and/or floating joint-function carrier/coating agent, or a joint-function carrier/coating agent, an additional coating agent, and a bioactive agent can be developed to distribute a bioactive agent to desired areas or volumes of a water column over time, or to one or more terrestrial organisms over time. Especially suitable joint-function carrier/coating agents comprise polyvinyl alcohol, polyethylene oxide, hydroxypropyl methyl cellulose, cetyl alcohol or stearyl alcohol and various combinations thereof such as the two, three or four component combinations.

All compositions can be optionally combined with a binder to agglomerate the composition into larger units such as granules, pellets, and briquets, or an additional formulation ingredient. In addition, all compositions can also be optionally dispensed in a water column enclosed within water soluble film containers, and/or dispensed from devices having one or more orifices open.

From these descriptions, it is obvious that one or more floating, and/or sinking carriers, coatings, and bioactive agents with or without binders or additional formulation ingredients can be combined in various permutations, and combinations into controlled release compositions that are designated to target desired areas or volume segments of a water column or an entire water column to treat a population of one or more aquatic organisms.

It should be noted in this regard that the water column is defined as a volume of water underneath the surface of water of a specified area that requires treatment, the body of water including ponds, lakes, bays, wetlands, marshes, swamps, tidal basins, lagoons, sounds, creeks, streams, rivers, oceans, ditches, swales, sewage treatment controlled delivery systems, potholes, tree holes, rock holes, bromeliads, tires, which is to say moving or stagnant water containing one or more target organisms. Thus, the treated column of water can be either moving or stationary, and have any water quality that can be utilized as a habitat for the target organism(s).

By treating a column of water, as that term is employed herein, it is intended not only to provide the compositions of matter of the present invention to a column of water that is infested with aquatic organisms that exist in the column, but also a column of water that has the potential of being infested with aquatic organisms. Compositions of matter of the present invention are also provided for pretreatment application to a dry habitat that has not yet flooded by rain, tides, and the like, to produce a defined water column where aquatic organisms are known to breed, i.e. a preflood area. Compositions of matter for pretreatment of an existing water column that is not yet infested with aquatic organisms or that are infested with organisms are also within the scope of the invention.

Compositions of matter are also provided, for treating terrestrial organisms in a land mass. A land mass can include any natural or artificial surface or subsurface area of a terrestrial environment.

The compositions of the present invention can be applied by ground or aerial techniques in any form such as liquids powders, granules, agglomerates, pellets, and briquets. These forms can be encapsulated within water soluble or porous, or degradable pouches, capsules, films or sheets, which may comprise polyvinyl alcohol, polyethylene oxide, hydroxypropyl methyl cellulose, paper, or gelatin, and/or within devices having one or more orifices in contact with the water column or land mass. The compositions of the present invention can also be applied as water, and/or oil based formulations.

In the following examples powdered and agglomerated controlled delivery compositions of matter are utilized as examples to illustrate the present invention, and were designed to target surface, subsurface, or both surface, and subsurface areas of an aquatic habitat. Larvae of Anopheles spp. mosquitoes were used as models to demonstrate the efficacy of surface active compositions, while larvae of Aedes spp. and Culex spp. mosquitoes were used to demonstrate subsurface efficacy.

Insecticidal bioactive agents admixed with a variety of carriers and coatings or joint-function carrier/coatings, with or without binders or formulating materials, were commercial formulations of the bacteria *Bacillus thuringiensis* var. *israelensis* (B.t.i.) (Acrobe® Technical Powder, Acrobe® Biolarvicide or Vectobac® Technical Powder), the insect growth regulators methoprene (Dianex® Emulisifiable Concentrate), pyriproxyfen (Nylar® Technical or Emulsifiable Concentrate), a mixture of Acrobe® TP, and Dianex® EC, the organophosphate temephos(Abater 4-E) or an experimental monomolecular surface film (POE(2) 2 mol ethoxylate of isostearyl Alcohol). Additional insecticidal bioactive agents admixed with a variety of coatings and carriers, with or without binders or formulation materials, that were not utilized in mosquito bioassays, were commercial formulations of the insect growth regulators diflubenzuron (Dimilin® Wettable Powder) the bacteria *Bacillus sphaericus* (ABG-6184), the fungus *Lagenidium giganteum,* and the petroleum oil (GB-1111). Examples of liquid or solid coatings utilized in the compositions of matter to regulate the controlled release rate and release profile of the bioactive agent(s) from the carrier were esters of citrate (Citroflex®2, A-2, 4, A-4, A-6 or B-6), phthalate, glycolate, trimellitate (Morflex® 150, 190, or 560), cetyl alcohol, and/or polyvinyl alcohol films (MonoSol® 7000 or 8000 series). Coatings ranged from water soluble to insoluble, and had specific gravities less than or greater than one. Solid carriers utilized in the compositions of matter as surface or subsurface-active bioactive agent delivery matrices were hydrophobic (Sipernat®D17, and Aerosil®R972) or hydrophilic (Wesslon™, Wesslon™ 50, Sipernat®22S, and FK 500 LS) Degussa silicas, sand (Texblast®), cetyl alcohol (Sigma®) (specific gravity less than one), and/or corn cob granules, BIODAC® granules and/or polyvinyl alcohol films (MonoSol®7000 or 8000 series) (specific gravity greater than one). Polymeric binders utilized in the examples to agglomerate the powdered compositions into larger units were soluble starch (Difco®), sulfonated polystyrene (Versa®TL-502), sulfonated vinylic copolymers (Narlex® D-82), acrylic copolymer (Carboset®514H), and acrylic i polymer (Carbopol®ETD 2001 Resin). Additional formulation materials such as water, soluble or insoluble alcohols (2-propanol, 2-ethyl hexanol, 2 mol ethoxylate of isostearyl alcohol) or ketones (acetone, methyl ethyl ketone) were also utilized as admixture components in selected compositions.

A series of bioassays were designed to demonstrate the short or long-term mosquito-controlling effectiveness of a variety of powdered and agglomerated compositions that were formulated to time-release one or more mosquitocidal bioactive agents in specific areas of a water column or the entire water column. Composition transfer bioassays were utilized to evaluate the controlled release duration of selected powdered, granular or agglomerated formulations. The efficacy of pretreatment compositions was also evaluated. Powdered, granular or agglomerated compositions were evaluated at ca. 27° C. in 0.019m$^2$ ½ gal plastic containers containing 1000 ml of fresh water (purified by reverse osmosis filtration) or brackish (10% Instant Ocean®/distilled water) water and ten 1st to 4th instar larvae of the Anopheles, Aedes, or Culex species. Bioassays were also conducted with mixed species populations. Tests with each powdered, granular or agglomerated controlled delivery composition were replicated three times.

The following examples are illustrative of the controlled delivery fabrication protocols, types of powdered, granular, agglomerated or extruded controlled release compositions, and processes for treating a population of aquatic or terrestrial organisms in a column of water or on land.

EXAMPLE 1

The admixing protocol for the components utilized in the powdered composition (Code J) in this bioassay series against mosquito larvae was as follows: 10 g cetyl alcohol (heated to 60° C.) and 5 g triethyl citrate (Citroflex®2) were each added separately to 300 g acetone in ½ gal plastic beakers and mixed with a laboratory hand mixer (GE® Model 420A) for ca. 5 minutes. 5 g of B.t.i. (Acrobe®TP) was then slowly added to each coating formulation while mixing for an additional 5 minutes. 85 g and 90 g hydrophobic silica (Sipernat®D17) were slowly added to the cetyl alcohol and triethyl citrate formulations of bacteria, respectively, while mixing for an additional 2½–3 hr to drive off the acetone and assure that the B.t.i. and each coating were uniformly impregnated on the silica carrier. Powdered compositions were placed in a low humidity room (27–38% RH; 76–79° F.) for an additional 4 hr to assure volatilization of the acetone. Each powdered formulation was stored in Zip-lock™ bags or glass bottles. Sub samples of each of the two formulations were admixed at a 1:1 ratio for an additional 5 minutes to achieve the powdered composition utilized for testing.

Results of short-term bioassays against Anopheles, Aedes, and Culex species in fresh or brackish water with a powdered controlled delivery composition comprising a 1:1 blend of an acetone-base (300 g) admixture formulation (w/w) of 5 g of B.t.i. (specific gravity greater than one/insoluble in water) labeled Acrobe®TP (3864 ITU/mg), 10 g cetyl alcohol (specific gravity less than one/insoluble in water), and 85 g hydrophobic silica (Sipernat®D17) and another acetone-base (300 g) admixture formulation (w/w) of 5 g Acrobe®TP, 5 g triethyl citrate (Citroflex®2; specific gravity greater than one/water soluble), and 90 g Sipernat®D17 indicated that the multiply coated/encapsulated B.t.i. could be released from the hydrophobic silica carrier at varying intervals/rates and provide effective control of both surface and subsurface feeding mosquito larvae at extrapolated application rates of ca. 2.5 lb/surface acre of water (Table 1). The efficacy of the composition against the Anopheles species indicated that Acrobe®TP can be maintained at the surface feeding area of an aquatic habitat for a sufficient period of time to effectively allow the Anopheles larvae to ingest lethal concentrations of toxic crystals of B.t.i. Efficacy against Aedes and Culex species suggested that the dense B.t.i. was slowly released from the surface-active carrier/coating formulation below the surface of the water through the water column where the toxic crystals were accessible to the subsurface and bottom feeding species. In general, the powdered controlled delivery composition was effective in releasing sufficient concentrations of B.t.i. over a 1 to 5 day posttreatment period to produce 100% control of surface or at subsurface feeding mosquito larvae in fresh or brackish water. Controlled release of B.t.i. from the silica carrier to surface and/or subsurface areas of a water column was a function of the type and concentration of coating agents. The initial point of B.t.i. release and distribution at the water interface was a function of the hydrophobic nature of the carrier.

TABLE 1

(Example 1). Coating-Regulated Delivery of Acrobe ® TP from a Hydrophobic Silica Carrier*

| Mosquito Species | Larval Instar | Water Quality | % Control of Larvae at Indicated Post-treatment Time Period (Days)** 1 | 2 | 3 | 4 | 5 |
|---|---|---|---|---|---|---|---|
| Surface Feeders (Anopheles spp.) | | | | | | | |
| *An. albimanus* | 2nd | Fresh | 100.0 | — | — | — | — |
| *An. albimanus* | 3rd | Fresh | 83.3 | 90.0 | 100.0 | — | — |
| *An. albimanus* | 4th | Fresh | 23.3 | 60.0 | 80.0 | 100.0 | — |
| *An. albimanus* | 2nd | Brackish | 90.0 | 100.0 | — | — | — |
| *An. albimanus* | 3rd | Brackish | 83.3 | 96.7 | 100.0 | — | — |
| *An. albimanus* | 4th | Brackish | 53.3 | 76.7 | 96.7 | 100.0 | — |
| *An. quadrimaculatus* | 2nd | Fresh | 100.0 | — | — | — | — |
| *An. quadrimaculatus* | 3rd | Fresh | 70.0 | 100.0 | — | — | — |
| *An. quadrimaculatus* | 4th | Fresh | 50.0 | 50.0 | 53.3 | 96.7 | 100.0 |
| Subsurface Feeders (Aedes and Culex spp.) | | | | | | | |
| *Ae. aegypti* | 1st | Fresh | 100.0 | — | — | — | — |
| *Ae. aegypti* | 3rd | Fresh | 53.3 | 90.0 | 100.0 | — | — |
| *Ae. taeniorhynchus* | 3rd | Brackish | 90.0 | 93.3 | 96.7 | 100.0 | — |
| *Cx. quinquefasciatus* | 3rd | Fresh | 26.7 | 43.3 | 83.3 | 100.0 | — |

*5% Acrobe ® TP (w/w) utilized in the controlled release composition. Cetyl alcohol and triethyl citrate utilized as B.t.i. release-rate regulators (formulation ratio of 1 part cetyl alcohol/B.t.i. to 1 part triethyl citrate/B.t.i.).
**B.t.i. compositions applied as a powder at ca. 2.5 lb/acre.

EXAMPLE 2

Another series of bioassays with other types of powdered controlled release compositions were conducted against larvae of Anopheles, Aedes, and mixed populations of Anopheles and Culex species in fresh and brackish water. In formulating these compositions of matter, B.t.i. (Acrobe®TP) was admixed with other types of hydrophobic (Aerosil®R972) and/or hydrophilic (FK 500 LS) silica, hydrophobic wood "pin chips" or saw dust (Sea Sweep®), or sand (Texblast®) carriers and cetyl alcohol and/or triethyl citrate (Citroflex® 2) coating agents into powdered controlled delivery compositions that had an affinity for targeting selected areas of an aquatic habitat (Table 2).

Results of a series of short-term bioassays with these powdered controlled release compositions are presented in Table 3. The data indicated that the type(s) of powdered carrier(s) (e.g., hydrophobic and/or hydrophilic) and the type(s) and concentration of coating/encapsulation agent(s) e.g., specific gravity greater than and/or less than one/water soluble and/or insoluble) utilized in a powdered composition would dictate the orientation of delivery in a water column and the rate of release of larvicidal bacteria. All powdered compositions provided 100% control of larvae in fresh or brackish water. In general, results indicated that specific carriers and coatings could be combined with B.t.i. in a manner to selectively target subsurface/bottom feeding mosquito larvae or mixed populations of surface and subsurface/bottom feeding mosquito larvae. The type of carrier was observed to initially orient the bioactive agent (i.e., B.t.i.) in a surface or subsurface plane of the water column while the type of coating agents would dictate controlled release persistence, rate, direction, and/or a change in the initially observed surface or subsurface release plane of B.t.i.

TABLE 2

(Example 2). Formulation Components in Powdered Controlled Delivery Compositions*

| Composition No. | Concentration of Admixtures in Powdered Compositions |
|---|---|
| 1 | 5 g B.t.i. (Acrobe ®TP) + 5 g cetyl alcohol + 5 g triethyl citrate (Citroflex ®2) + 42.5 g hydrophobic silica (Aerosil ® R972) + 42.5 g hydrophilic silica (FK 500 LS) |
| 2 | 5 g B.t.i. (Acrobe ®TP) + 10 g cetyl alcohol + 85 g hydrophilic silica (FK 500 LS) |
| 3 | 10 g B.t.i. (Acrobe ®TP) + 10 g triethyl citrate (Citroflex ® 2) + 180 g hydrophobic "pin chips" (Sea Sweep ®) |
| 4 | 5 g B.t.i. (Acrobe ®TP) + 20 g cetyl alcohol + 75 g sand (Texblast ®) |

*Cetyl alcohol (heated to 60° C.) and/or triethyl citrate was added to 300 g acetone and mixed for 5 minutes with a GE ® Model 420A hand mixer in a 1/2 gal plastic beaker. B.t.i. was slowly added to solvent-base formulation of coating(s) while mixing for an additional 5 minutes. Hydrophobic and/or hydrophilic silica or sand was ad-mixed with the other components while mixing was continued for ca. 3 hr to drive off the acetone and assure a homogeneous dry mixture of all the components.
Hydrophobic "pin chips" were ground with a Micro-Mill ® into a fine powder. Tri-ethyl citrate was added to a stainless steel bowl containing 800 g acetone and mixed for ca. 5 minutes with a KitchenAid ® KSM 90 (speed #6) hand mixer. B.t.i. was added slowly and mixing was continued for ca. 5 minutes. Ground "pin chips" were slowly added to the mixture while blending was continued on speed #2 for ca. 4 hr until the powdered formulation was dry.
All powdered compositions were placed in a low-humidity room (ca. 27–38% RH) for ca. 3 hr to assure volatilization of the solvent. Powdered compositions were stored in zip-lock bags or glass bottles.

TABLE 3

(Example 2). Coating-Regulated Delivery of Acrobe ® TP From Several Types of Hydrophobic and Hydrophilic Carriers.*

| Mosquito Species | Larval Instar(s) | Water Quality | Composition No. | % Control of Larvae at Indicated Posttreatment Time Period (Days)** 1 | 2 | 3 | 4 | 5 | 6 | 7 |
|---|---|---|---|---|---|---|---|---|---|---|
| Subsurface Feeders (Aedes and Culex spp.) | | | | | | | | | | |
| *Ae. aegypti* | 2nd | Fresh | 1 | 76.7 | 90.0 | 96.7 | 100.0 | — | — | — |
| *Ae. aegypti* | 3rd | Fresh | 2 | 93.3 | 96.7 | 100.0 | — | — | — | — |
| *Ae. taeniorhynchus* | 3rd | Brackish | 1 | 90.0 | 100.0 | — | — | — | — | — |

TABLE 3-continued (Example 2). Coating-Regulated Delivery of Acrobe ® TP From Several Types of Hydrophobic and Hydrophilic Carriers.*

| Mosquito Species | Larval Instar(s) | Water Quality | Composition No. | % Control of Larvae at Indicated Posttreatment Time Period (Days)** 1 | 2 | 3 | 4 | 5 | 6 | 7 |
|---|---|---|---|---|---|---|---|---|---|---|
| *Ae. taeniorhynchus* | 3rd | Brackish | 2 | 63.3 | 90.0 | 100.0 | — | — | — | — |
| *Ae. taeniorhynchus* | 3rd | Brackish | 3 | 40.0 | 83.3 | 96.7 | 96.7 | 100.0 | — | — |
| *Cx. quinquefasciatus* | 3rd | Fresh | 1 | 63.3 | 83.3 | 96.7 | 100.0 | — | — | — |
| *Cx. quinquefasciatus* | 3rd | Fresh | 3 | 93.3 | 100.0 | — | — | — | — | — |
| *Cx. quinquefasciatus* | 4th | Fresh | 1 | 100.0 | — | — | — | — | — | — |
| *Cx. quinquefasciatus* | 4th | Fresh | 2 | 100.0 | — | — | — | — | — | — |
| Subsurface/Surface Feeders (Culex and Anopheles spp.)*** | | | | | | | | | | |
| *Cx. quinquefasciatus/ An. albimanus* | 3rd/2nd | Fresh | 2 | 83.3 | 93.3 | 93.3 | 96.7 | 100.0 | — | — |
| *Cx. quinquefasciatus/ An. albimanus* | 3rd/2nd | Fresh | 4 | 50.0 | 63.3 | 66.7 | 90.0 | 90.0 | 93.3 | 100.0 |

*5% Acrobe ® TP utilized in all controlled release compositions. Cetyl alcohol and/or triethyl citrate utilized as B.t.i. release-rate regulators.
**B.t.i. compositions applied as a powder at ca. 2.5 lb/acre.
***Mixed Culex and Anopheles larvae (1:1).

EXAMPLE 3

Powdered admixtures of B.t.i. (Acrobe®TP), a hydrophobic silica (Sipernat®D17) carrier, a cetyl alcohol coating, and a soluble starch, sulfonated polystyrene (Versa®TL-502) or sulfonated vinylic (Narlex®D-82) polymeric binder were also agglomerated by hand into a series of controlled delivery briquets (Table 4). Small cubettes (ca. 3.5×3.5×4.5 mm) were sectioned from each type of B.t.i. briquet and utilized in a series short-term bioassays against 2nd instar larvae of Anopheles and Culex species in fresh and brackish water. One cubette per bioassay test chamber (i.e., plastic ½ gal beakers) was equivalent to an extrapolated application rate of ca. 5 lb/surface acre of water.

Evaluation of 3 types of Acrobe®TP cubettes against Anopheles and Culex larvae indicated that the rate of control was a function of the coating-regulated release of B.t.i. from the encapsulated silica and the rate of binder-regulated dissociation of the powdered components from the agglomerated matrices in fresh or brackish water (Table 5). Observations indicated that the initial orientation of the Narlex®, soluble starch, and Versa® cubettes on introduction to water was sinks, sinks, and floats, respectively. Dissociation of Narlex® and Versa® cubettes into smaller powder-like components occurred in ca. 5 minutes after introduction into the fresh or brackish water, while soluble starch cubettes dissociated into several small subagglomerated units in about 24 hr after introduction to fresh or brackish water. The smaller subagglomerated units were observed to dissociate into still smaller powder-like components over a several day period. The hydrophobic silica carrier coated with the insoluble, low specific gravity cetyl alcohol and B.t.i. was observed to float upon being released from the initial surface or subsurface orientation of the cubette in the aquatic habitat. The series of agglomerated B.t.i. compositions produced 100% control of larvae within 1 to 9 days posttreatment.

TABLE 4

(Example 3). Formulation Components in Agglomerated Controlled Delivery Compositions*

| Composition Code | Concentration of Admixtures in Agglomerated Compositions |
|---|---|
| A | 5 g 5 g B.t.i. (Acrobe ®TP) + 10 g cetyl alcohol + 85 g hydrophobic silica (Sipernat ®D17) + 5 g sulfonated polystyrene polymer (Versa ®TL-502) |
| B | 5 g 5 g B.t.i. (Acrobe ®TP) + 10 g cetyl alcohol + 85 g hydrophobic silica (Sipernat ®D17) + 5 g sulfonated vinylic copolymer (Narlex ®D-82) |
| C | 5 g 5 g B.t.i. (Acrobe ®TP) + 10 g cetyl alcohol + 85 g hydrophobic silica (Sipernat ®D17) + 5 g soluble starch |

*Cetyl alcohol (heated to 60° C.) was added to 300 g acetone and mixed for ca. 5 minutes with a GE ® Model 420A hand mixer in a 1/2 gal plastic beaker. B.t.i. was slowly added into the solvent-base formulation of coating while mixing for an additional 5 minutes. Hydro-phobic silica was mixed with the other components while mixing was continued for ca. 3 hr to drive off the acetone and assure a homogeneous dry mixture of all components. The powdered composition was placed in a low humidity room (ca. 27–38% RH) for ca. 4 hr to assure volatilization of solvent. A ratio of one part of this powdered 3-part bioactive agent/coating/carrier formulation was mixed with one part binder (sulfonated polystyrene polymer, sulfonated vinylic copolymer or soluble starch) for ca. 5 minutes. The 1:1 composition was then hand compacted into 25 × 20 × 5 mm vinyl specimen molds (Cryomold ®) and placed in a high humidity curing room (ca. 80% RH and 80° F.) for ca. 96 hr. Molds containing each composition were then transferred to a drying room (ca. 27–38% RH, 76–79° F.) for an additional 96 hr. The dry solidified briquet compositions in each mold were stored in plastic zip-lock bags. Subsections of each briquet (i.e., ca. 3.5 × 3.5 × 4.5 mm cubettes) were utilized in the bioassays. One cubette (ca. 0.01 g) was utilized against mosquito larvae in each bioassay test chamber (3 replications/agglomerated composition).

TABLE 5

(Example 3). Coating-Regulated Delivery of Acrobe ® TP from Agglomerated Compositions*

| Mosquito Species | Water Quality | Composition Code | % Control of 2nd Instar Larvae at Indicated Posttreatment Time Period (Days)** | | | | | | | | |
|---|---|---|---|---|---|---|---|---|---|---|---|
| | | | 1 | 2 | 3 | 4 | 5 | 6 | 7 | 8 | 9 |
| Surface Feeders (Anopheles spp.) | | | | | | | | | | | |
| *An. albinanus* | Fresh | A | 93.3 | 100.0 | — | — | — | — | — | — | — |
| *An. albimanus* | Fresh | B | 100.0 | — | — | — | — | — | — | — | — |
| *An. albimanus* | Brackish | A | 90.0 | 100.0 | — | — | — | — | — | — | — |
| *An. albimanus* | Brackish | B | 90.0 | 100.0 | — | — | — | — | — | — | — |
| *An. albimanus* | Brackish | C | 16.7 | 33.3 | 33.3 | 43.3 | 86.7 | 96.7 | 100.0 | — | — |
| *An. quadrimaculatus* | Fresh | A | 93.3 | 100.0 | — | — | — | — | — | — | — |
| *An. quadrimaculatus* | Fresh | B | 96.7 | 100.0 | — | — | — | — | — | — | — |
| Subsurface Feeders (Culex spp.) | | | | | | | | | | | |
| *Cx. quinquefasciatus* | Fresh | A | 100.0 | — | — | — | — | — | — | — | — |
| *Cx. quinquefasciatus* | Fresh | B | 93.3 | 100.0 | — | — | — | — | — | — | — |
| *Cx. quinquefasciatus* | Fresh | C | 23.3 | 43.3 | 63.3 | 70.0 | 83.3 | 86.7 | 90.0 | 96.7 | 100.0 |

*5% Acrobe ® TP (w/w) utilized in each agglomerated controlled release B.t.i. composition. Compositions contained B.t.i., a cetyl alcohol coating, a hydrophobic silica carrier, and a sulfonated polystyrene polymer, sulfonated vinylic copolymer, or soluble starch binder (formulation ratio of 1 part bioactive agent/coating/carrier to 1 part binder).
**B.t.i. compositions applied as an agglomerated cubette at ca. 5 lb/acre.

EXAMPLE 4

A controlled delivery system for solvent-base (i.e., acetone) precipitation was developed to agglomerate an aqueous admixture suspension of a joint-function carrier/coating water soluble polyvinyl alcohol film (MonoSol® 8000 series) and B.t.i. (Acrobe® Biolarvicide). The procedure utilized a series of acetone washes to rapidly congeal the aqueous homogeneous mixture of polyvinyl alcohol film and B.t.i. into a unified mass by removing the water entrapped within the solid. Polyvinyl alcohol films (specific gravity greater than one) are soluble in water and insoluble in acetone while B.t.i. is suspendible in water but insoluble in acetone or water.

Compositions were prepared utilizing the following protocol: 12 g polyvinyl alcohol film (MonoSol® 8000 series) was dissolved in 46.8 g distilled water in a plastic beaker. 1.2 g Acrobe® Biolarvicide was mixed with the water-base joint-function carrier/coating with a GE® 420A hand mixer for ca. 2 minutes. The formulation was poured into 2 ounce glass medicine bottles and vigorously hand shaken for ca. 1 minute. 7 to 10 g polyvinyl alcohol film/B.t.i/water formulation was added to a plastic centrifuge tube (ca. 60 ml capacity) containing ca. 35–40 g acetone. The centrifuge tube was capped and vigorously hand shaken to solidify the polyvinyl alcohol film and B.t.i. into a unified mass within the aqueous-acetone medium. The solid mass was removed and placed into 50 ml glass beakers containing ca. 40 g acetone for a series of five one minute washes to remove entrapped water from within the solid matrix. The solid mass was removed from the acetone and thoroughly air-dried in a low humidity room (ca. 27–38% RH) for ca. 72 hr. The solid compositions were stored in Zip-lock™ bags until bioassay. The remaining stock formulation of water, polyvinyl alcohol film, and B.t.i. was stored in a refrigerator (ca. 40° F.) for future use.

A series of short-term bioassays were conducted against larvae of Anopheles, Aedes, and Culex species in fresh and brackish water with 2×2×2 mm cubettes that were sectioned from each agglomerated mass of polyvinyl alcohol film and B.t.i. (Table 6). An application rate of one cubette (ca. 0.01 g) per bioassay test chamber (i.e., ½ gal plastic beaker) was extrapolated to be ca. 5 lb/surface acre of water (3 replications/test). Results indicated that 100% control of surface or subsurface feeding larvae could be achieved in fresh or brackish water within 1 to 5 days posttreatment. Based on the specific gravity of the components, cubettes were expected to sink upon introduction to fresh and brackish water. However, observations indicated that the agglomerated polyvinyl alcohol film compositions initially floated and began to solubilize over a 24 hr period, thereby rapidly releasing significant quantities of B.t.i. from the surface to subsurface areas while also retaining B.t.i. in the polyvinyl alcohol film that had spread over the surface of the water. It appears that air bubbles entrapped within the polyvinyl alcohol film matrix during the vigorous admixing procedure in combination with the suspending agents/surfactants present in the Acrobe® Biolarvicide formulation were responsible for the initial surface orientation of the cubettes, and the film-forming properties of the water soluble cubettes. The data on the rates of mortality of surface (i.e., Anopheles spp.) and subsurface (i.e., Aedes and Culex spp.) feeding larvae support the aforementioned observations concerning film-forming solubilization of cubettes and release of B.t.i in the experimental aquatic habitats.

TABLE 6

(Example 4). Coating-Regulated Delivery of Acrobe ® Biolarvicide from an Agglomerated Joint-Function Composition*

| Mosquito Species | Larval Instar | Water Quality | % Control of Larvae at Indicated Posttreatment Time Period (Days)** | | | | |
|---|---|---|---|---|---|---|---|
| | | | 1 | 2 | 3 | 4 | 5 |
| Surface Feeders (Anopheles spp.) | | | | | | | |
| *An. albimanus* | 2nd | Fresh | 70.0 | 76.7 | 100.0 | — | — |
| *An. albimanus* | 2nd | Brackish | 46.7 | 50.0 | 100.0 | — | — |
| *An. albimanus* | 3rd | Fresh | 40.0 | 46.7 | 90.0 | 100.0 | — |
| *An. albimanus* | 3rd | Brackish | 43.3 | 46.7 | 100.0 | — | — |

TABLE 6-continued (Example 4). Coating-Regulated Delivery of Acrobe ® Biolarvicide from an Agglomerated Joint-Function Composition*

| Mosquito Species | Larval Instar | Water Quality | % Control of Larvae at Indicated Posttreatment Time Period (Days)** 1 | 2 | 3 | 4 | 5 |
|---|---|---|---|---|---|---|---|
| *An. quadrimaculatus* | 2nd | Fresh | 93.3 | 93.3 | 100.0 | — | — |
| *An. quadrimaculatus* | 3rd | Fresh | 30.0 | 30.0 | 66.7 | 90.0 | 100.0 |
| Subsurface Feeders (Aedes and Culex spp.) | | | | | | | |
| *Ae. taeniorhynchus* | 2nd | Brackish | 100.0 | — | — | — | — |
| *Ae taeniorhynchus* | 3rd | Brackish | 100.0 | — | — | — | — |
| *Cx. quinquefasciatus* | 2nd | Fresh | 100.0 | — | — | — | — |
| *Cx. quinquefasciatus* | 3rd | Fresh | 100.0 | — | — | — | — |

*9% Acrobe ® Biolarvicide (w/w) in each controlled release B.t.i. composition. Compositions contained a water and solvent-free joint-function carrier/coating polyvinyl alcohol film (91%) and bioactive agent 9%.
**B.t.i. compositions applied as agglomerated cubettes at ca. 5.0 lb/acre.

EXAMPLE 5

A series of short-term controlled release bioassays were also conducted against larvae of Anopheles, Aedes, and Culex species in fresh and brackish water to determine the mosquito-controlling efficacy of powdered compositions comprising admixtures of B.t.i. (Vectobac® TP), the insect growth regulator methoprene (Dianex®EC), a joint-action formulation of Dianex®EC and B.t.i. (Acrobe®TP) or an organophosphate (Abate®4-E) and a cetyl alcohol coating and hydrophobic silica (Sipernat® D17) carrier. Abate® 4-E was also admixed with a water soluble polyvinyl alcohol film (MonoSol® 8000 series) joint-function carrier/coating to form a solid agglomerated composition that was sectioned into cubettes (ca. 3.5×3.5×4.5 mm). Admixing procedures for formulating these powdered or agglomerated controlled delivery compositions are presented in Table 7.

Results of bioassays with the powdered and cubette compositions indicated that controlled delivery of formulations of an organophosphate (specific gravity greater than one), insect growth regular (specific gravity less than one) and a bacteria (specific gravity greater than one)/insect growth regulator (specific gravity less than one) from a hydrophobic silica or joint-function polyvinyl alcohol film carrier was regulated by the physico-chemical characteristics of the cetyl alcohol or polyvinyl alcohol film coatings admixed into the formulation (Table 8). The data indicated that the surface-active powdered or agglomerated (cubette) floating compositions were effective in delivering at varying rates one or more bioactive agents at and/or below the surface of the water where Anopheles, Aedes, and Culex species could be targeted by the specific type(s) of bioactive agent(s) released from the carrier into different vertical and horizontal areas of the water column. One hundred percent control of all immature mosquitoes was observed within 1 to 21 days posttreatment when the compositions were applied as a direct treatment or pretreatment in fresh or brackish water at an extrapolated rate of 2.5 lb/surface acre of water for powdered compositions and 5.0 lb/surface acre of water for agglomerated compositions.

TABLE 7

(Example 5). Formulation Components in Powdered and Agglomerated Controlled Delivery Compositions

| Composition Code | Concentration of Admixtures in Powdered and Agglomerated Compositions |
|---|---|
| | Powdered Compositions* |
| D | 0.5 g methoprene (Dianex ®EC) + 10 g cetyl alcohol + 89.5 g hydrophobic silica (Sipernat ®D17) |
| E | 5 g 0.5 g methoprene (Dianex ®EC) + 10 g cetyl alcohol + 89.5 g hydro-phobic silica (Sipernat ®D17) + 5 g 5 g B.t.i. (Acrobe ®TP) + 10 g cetyl alcohol + 85 g hydrophobic silica (Sipernat ®D17) |
| F | 5 g B.t.i. (Vectobac ®TP) + 10 g cetyl alcohol + 85 g hydrophobic silica (Sipernat ®D17) |
| G | 0.5 g temephos (Abate ®4-E) + 10 g cetyl alcohol + 89.5 g hydrophobic silica (Sipernat ®D17) |
| | Agglomerated Compositions** |
| H | 0.3 g temephos (Abate ®4-E) + 12 g polyvinyl alcohol film (MonoSol ®8000 series) + 47.7 g distilled water + acetone bath series |

*Cetyl alcohol (heated to 60° C.) was added to 300 g acetone and mixed for ca. 5 minutes with a GE ® odel 420A hand mixer in a 1/2 gal plastic beaker. B.t.i., methoprene or methoprene and B.t.i. or temephos was slowly added to the solvent-base formulations of coating while mixing for an additional 5 minutes. Hydrophobic silica was added to each solvent-base bioactive agent/coating formulation while mixing was continued for ca. 3 hr to drive off the acetone and assure that the silica was uniformly encapsulated with the homogeneous mixture of each bioactive agent and coating. Two bioactive agents were combined into a single formulation by admixing each bioactive agent/coating/carrier formulation at a 1:1 mixing ratio. Each powdered composition was placed in a low humidity room (ca. 27–38% RH) for ca. 4 hr to assure volatilization of the solvent. The dry powdered compositions were stored in zip-lock bags or glass bottles until being utilized in mosquito bioassays.
**Polyvinyl alcohol film was dissolved in distilled water in a plastic beaker. Temephos was mixed with the aqueous formulation of joint-function coating/carrier with a GE ® Model 420A hand mixer for ca. 2 minutes. The insecticide formulation was poured into 2 ounce glass medicine bottles and vigorous shaken by hand for ca. 1 minute. 7–10 g water-base polyvinyl alcohol film/temephos formulation was added into a plastic centrifuge tube (ca. 60 ml capacity) containing ca. 35–40 g acetone. The centrifuge tube was capped and vigorous hand shaken to solidify the polyvinyl alcohol film and B.t.i. admixture into a unified mass within the aqueous-acetone medium. The solid mass was removed and placed into 50 ml glass beakers containing ca. 40 g acetone for a series of five one minute washes to remove entrapped water from within the solid matrix. The solid mass was removed from the acetone and thoroughly air-dried in a low humidity room (ca. 27–38% RH) for ca. 72 hr. The solid compositions were stored in zip-lock bags or glass bottles until being used for mosquito bioassays. Remaining stock formulation of water, polyvinyl alcohol, and temephos was stored in a refrigerator (ca. 40° F.) for future use.

TABLE 8

(Example 5). Coating-Regulated Delivery of Dianex ® EC, Dianex ® EC/Acrobe ® TP, Vectobac ® TP or Abate ® 4-E from Powdered or Agglomerated Compositions*

| Mosquito Species | Larval Instar | Water Quality | No. Days to Achieve 100% Control of Larvae, Pupae, and/or Emerging Adults |
|---|---|---|---|
| Powdered Composition - Dianex ® EC (0.5% AI Formulation) - Code D | | | |
| *An. albimanus* | 1st | Fresh | 21** |
| *An. albimanus* | 1st | Brackish | 20** |
| *Ae. aegypti* | 3rd | Fresh | 16 |
| *Ae. taeniorhynchus* | 3rd | Brackish | 14 |

TABLE 8-continued (Example 5). Coating-Regulated Delivery of Dianex ® EC, Dianex ® EC/Acrobe ® TP, Vectobac ® TP or Abate ® 4-E from Powdered or Agglomerated Compositions*

| Mosquito Species | Larval Instar | Water Quality | No. Days to Achieve 100% Control of Larvae, Pupae, and/or Emerging Adults |
|---|---|---|---|
| Powdered Composition - Dianex ® EC/Acrobe ® TP (0.5%/5% AI 1:1 Formulation) - Code E | | | |
| *Ae. taeniorhynchus* | 3rd | Brackish | 4 |
| *Cx. quinquefasciatus* | 3rd | Fresh | 18 |
| Powdered Composition - Vectobac ® TP (5% AI Formulation) - Code F | | | |
| *Cx. quinquefasciatus* | 2nd | Fresh | 10 |
| Powdered Composition - Abate ® 4-E (0.5% AI Formulation) - Code G | | | |
| *An. albimanus* | 1st | Fresh | 1 |
| *An. albimanus* | 1st | Fresh | 2** |
| *An. albimanus* | 1st | Brackish | 1 |
| *An. albimanus* | 1st | Brackish | 2** |
| *Ae. taeniorhynchus* | 3rd | Brackish | 1 |
| *Cx. quinquefasciatus* | 3rd | Fresh | 1 |
| Agglomerated Composition - Abate ® E (0.5% AI Aqueous/2.4% AI Dry Formulation) - Code H | | | |
| *An. albimanus* | 4th | Fresh | 1 |
| *An. albimanus* | 4th | Brackish | 1 |
| *An. quadrimaculatus* | 4th | Fresh | 1 |
| *Ae. taeniorhynchus* | 3rd | Brackish | 1 |
| *Cx. quinquefasciatus* | 2nd | Fresh | 1 |

*Powdered controlled release compositions consisted of a cetyl alcohol coating, bioactive agent(s), and hydrophobic silica carrier. Agglomerated (cubette) controlled release compositions consisted of a water and solvent-free joint-function poly-vinyl alcohol film coating/carrier (97.6%) and bioactive agent (2.4%). Powdered and agglomerated compositions applied to the water at rates of 2.5 and 5.0 lb/acre, respectively.
**Presoaked (pretreatment) in water for 9 days before transfer to bioassay containers.

EXAMPLE 6

A series of long-term controlled release transfer-bioassays were conducted against multiple broods of larvae of Anopheles, Aedes, and Culex species in fresh or brackish water with a variety of powdered or agglomerated compositions composed of one or more bioactive agents having differential degrees of specific gravity greater than or less than one, one or more coating shaving specific gravities with differential degrees of greater than or less than one as well as differential degrees of water solubility or insolubility, and a carrier having hydrophobic or hydrophilic characteristics, with or without a binder component. Carrier components consisted of either a hydrophobic silica (Sipernat® D17) or hydrophilic silica (FK 500 LS or Wesslon™ 50). Bioactive agents utilized in the admixture compositions were B.t.i. (Acrobe® TP), a combination of B.t.i. and methoprene (Dianex® EC) or temephos (Abate® 4-E). Coatings utilized as bioactive agent release rate and release profile regulators were cetyl alcohol (specific gravity less than one/insoluble in water), triethyl citrate (Citroflex® 2; specific gravity greater than one/water soluble), acetyltriethyl citrate (Citroflex® A-2; specific gravity greater than one/water soluble), tributyl citrate (Citroflex® 4; specific gravity greater than one/insoluble in water), acetyltributyl citrate (Citroflex® A-4; specific gravity greater than one/insoluble in water), a cetyltri-n-hexyl citrate (Citroflex® A-6; specific gravity greater than one/insoluble in water), n-butyltri-n-hexyl citrate (Citroflex B-6; specific gravity less than one/insoluble in water), dicyclohexyl phthalate (Morflex® 150; specific gravity greater than one/insoluble in water), butyl phthalyl butyl glycolate (Morflex®190; specific gravity greater than one/insoluble in water), and t ri-n-hexyl trimellitate (Morflex® 560; specific gravity greater than one/insoluble in water). Binders admixed with selected formulations to assist in agglomerating the fine components into larger units (e.g., briquets) were either a sulfonated polystyrene polymer (Versa® TL-502), a sulfonated vinylic copolymer (Narlex® D-82) or a water soluble starch. Components utilized in the admixing procedures to formulate the controlled release compositions are presented in Table 9.

Results of a series of long-term transfer bioassays in fresh and brackish water against several broods of larvae of Anopheles, Aedes, and Culex species with a variety of powdered and agglomerated (i.e., cubette) compositions of B.t.i. (Acrobe® TP) or methoprene (Dianex® EC) and B.t.i. have indicated that these controlled release compositions can be effective in slowly distributing lethal concentrations of a bacteria and/or insect growth regulator for a prolonged period to surface and/or subsurface areas of a water column that were readily accessible to the feeding and/or orientation of various species of larvae (Table 10). The data indicated that the direction(s), duration, and rate(s) of controlled release of the bioactive agent(s) in an aquatic habitat were functions of the surface or subsurface orientation of the carrier(s), and the type and concentration of coating(s) and bioactive agent(s) utilized in the powdered or agglomerated compositions. The results indicated that 100% control of multiple broods of larvae of Anopheles, Aedes or Culex species could be obtained in fresh or brackish water for at least 3–8 weeks when powdered or agglomerated compositions were applied to the water at rates of ca. 2.5 and 5.0 lb/acre, respectively. Powdered and agglomerated compositions were still producing 100% control of larval populations when tests were terminated.

Similar results were obtained against larvae of Aedes, Anopheles and Culex when corn cob granules and BIODAC® granules were used as carriers for the coating-regulated controlled delivery bioactive agent compositions.

TABLE 9

(Example 6). Formulation Components in Powdered and Agglomerated Controlled Delivery Compositions

| Composition Code/No. | Concentration of Admixtures in Powdered and Agglomerated Compositions |
|---|---|
| | Powdered Compositions* |
| J (Example 1) | 5 g 5 g B.t.i. (Acrobe ®TP) + 10 g cetyl alcohol + 85 g hydrophobic silica (Sipernat ®D17) + 5 g 5 g B.t.i. (Acrobe ®TP) + 5 g triethyl citrate (Citroflex ®2) + 90 g hydrophobic silica (Sipernat ®D17) |
| 2 (Example 2) | 5 g B.t.i. (Acrobe ®TP) + 10 g cetyl alcohol + 85 g hydrophilic silica (FK 500 LS) |
| K | 5 g B.t.i. (Acrobe ®TP) + 5 g triethyl citrate (Citroflex ®2) + 90 g hydrophilic silica (Wesslon ™50) |
| L | 5 g B.t.i. (Acrobe ®TP) + 5 g acetyltriethyl citrate (Citroflex ®A-2) + 90 g hydrophilic silica (Wesslon ™50) |
| M | 5 g B.t.i. (Acrobe ®TP) + 5 g tributyl citrate (Citroflex ®4) + 90 g hydrophilic silica (Wesslon ™50) |
| N | 5 g B.t.i. (Acrobe ®TP) + 5 g triethyl citrate (Citroflex ®2) + 90 g hydrophobic silica (Sipernat ®D17) |
| O | 5 g B.t.i. (Acrobe ®TP) + 5 g acetyltriethyl citrate (Citroflex ®A-2) + 90 g hydrophobic silica (Sipernat ®D17) |

TABLE 9-continued (Example 6).
Formulation Components in Powdered and Agglomerated Controlled Delivery Compositions

| Composition Code/No. | Concentration of Admixtures in Powdered and Agglomerated Compositions |
|---|---|
| P | 5 g B.t.i. (Acrobe ®TP) + 5 g tributyl citrate (Citroflex ®4) + 90 g hydrophobic silica (Sipernat ®D17) |
| Q | 5 g B.t.i. (Acrobe ®TP) + 5 g acetyltributyl citrate (Citroflex ®A-4) + 90 g hydrophobic silica (Sipernat ®D17) |
| R | 5 g B.t.i. (Acrobe ®TP) + 5 g acetyltri-n-hexyl citrate (Citroflex ®A-6) + 90 g hydrophobic silica (Sipernat ®D17) |
| S | 5 g B.t.i. (Acrobe ®TP) + 5 g n-butyltri-n-hexyl citrate (Citroflex ®B-6) + 90 g hydrophobic silica (Sipernat ®D17) |
| T | 5 g B.t.i. (Acrobe ®TP) + 2.5 g triethyl citrate (Citroflex ®2) + 2.5 g tributyl citrate (Citroflex ®4) + 90 g hydrophobic silica (Sipernat ®D17) |
| U | 5 g B.t.i. (Acrobe ®TP) + 5 g dicyclohexyl phthalate (Morflex ®150) + 90 g hydrophobic silica (Sipernat ®D17) |
| V | 5 g B.t.i. (Acrobe ®TP) + 5 g butyl phthalyl butyl glycolate (Morflex ®190) + 90 g hydrophobic silica (Sipernat ®D17) |
| W | 5 g B.t.i. (Acrobe ®TP) + 5 g tri-n-hexyl trimellitate (Morflex ®560) + 90 g hydrophobic silica (Sipernat ®D17) |
| E (Example 5) | 5 g 5 g B.t.i. (Acrobe ®TP) + 10 g cetyl alcohol + 85 g hydrophobic silica (Sipernat ®D17) + 5 g 0.5 g methoprene (Dianex ®EC) + 10 g cetyl alcohol + 89.5 g hydrophobic silica (Sipernat ®D17) |
| | Agglomerated Compositions** |
| A (Example 3) | 5 g 5 g B.t.i. (Acrobe ®TP) + 10 g cetyl alcohol + 85 g hydrophobic silica (Sipernat ®D17) + 5 g sulfonated polystyrene polymer (Versa ®TL-502) |
| B (Example 3) | 5 g 5 g B.t.i. (Acrobe ®TP) + 10 g cetyl alcohol + 85 g hydrophobic silica (Sipernat ®D17) + 5 g sulfonated vinylic copolymer (Narlex ®D-82) |
| C (Example 3) | 5 g 5 g B.t.i. (Acrobe ®TP) + 10 g cetyl alcohol + 85 g hydrophobic silica (Sipernat ®D17) + 5 g soluble starch |

*Cetyl alcohol (heated to 60° C.), triethyl citrate, a combination of triethyl citrate and cetyl alcohol, acetyltriethyl citrate, tributyl citrate, acetyltributyl citrate, acetyltri-n-hexyl citrate, n-butyltri-n-hexyl citrate, dicyclohexyl phthalate, butyl phthalyl butyl glycolate, tri-n-hexyl trimellitate, or a 1:1 combination of triethyl citrate and tributyl citrate was added to 300 g acetone and mixed for ca. 5 minutes (speed #6; wire whip) with a KitchenAid ®KSM 90 hand mixer in a 4 1/2 qt stainless steel bowl or with a GE ® hand mixer Model 420A. B.t.i. or a B.t.i. and methoprene mixture was slowly added to the solvent-base formulations of coatings while mixing (stir, speed #6, wire whip) was continued for ca. 5 minutes. Hydrophobic or hydrophilic silica was added to each solvent-base bioactive agent/coating formulation while mixing (stir, speed #6, wire whip, flat beater blade) was continued for ca. 3 hr to drive office the acetone and assure that the silica was uniformly encapsulated with the homogeneous mixture of each bioactive agent and coating. Two bioactive agents were combined into a single formulation by admixing each bioactive agent/coating/carrier formulation at a 1:1 mixing ratio. Each powdered composition was placed in a low humidity room (ca. 27–38% RH) for ca. 3 to 4 hr to assure volatilization of the solvent. The dry powdered compositions were stored in zip-lock bags or glass bottles until being utilized in mosquito bioassays.

**Cetyl alcohol (heated to 60° C.) was added to 300 g acetone and mixed for ca. 5 minutes with a GE ® Model 420A hand mixer in a 1/2 gal plastic beaker. B.t.i. was slowly added into the sol-vent-base formulation of coating while mixing for an additional 5 minutes. Hydrophobic silica was mixed with the other components while mixing was continued for ca. 3 hr to drive off the acetone and assure a homogeneous dry mixture of all components. The powdered composition was placed in a low humidity room (ca. 27–38% RH) for ca. 4 hr to assure volatilization of solvent. A ratio of one part of this powdered 3-part bioactive agent/coating/carrier formulation was mixed with one part binder (sulfonated polystyrene polymer, sulfonated vinylic copolymer or soluble starch) for ca. 5 minutes. The 1:1 composition was then hand compacted into 25 × 20 × 5 mm vinyl specimen molds (Cryomold ®) and placed in a high humidity curing room (ca. 80% RH and 80° F.) for ca. 96 hr. Molds containing each composition were then transferred to a drying room (ca. 27–38% RH, 76–79° F.) for an additional 96 hr. The dry solidified briquet compositions in each mold were stored in plastic zip-lock bags. Subsections of each briquet (i.e., ca. 3.5 × 3.5 × 4.5 mm cubettes) were utilized in the bioassays. One cubette (ca. 0.01 g) was utilized against mosquito larvae in each bioassay test chamber (3 replications/agglomerated composition).

TABLE 10

(Example 6). Coating-Regulated Controlled Delivery of Acrobe ® TP or Acrobe ® TP/Dianex ® EC from Powdered or Agglomerated Compositions*

| Mosquito Species | Larval Instar/Composition Transfer Period (T)** | Water Quality | Composition Code/No. | No. Days to Achieve 100% Larval Control at Composition Transfer Period (No. Days Between Transfers) Test Duration $T_0$ | $(T_0–T_1)$ | $T_1$ | $(T_1–T_2)$ | $T_2$ | (Days)*** |
|---|---|---|---|---|---|---|---|---|---|
| Powdered Compositions - ACROBE ® TP (5% AI Formulation) | | | | | | | | | |
| *Ae. aegypti* | 3rd/$T_0$, $T_1$ | Fresh | J | 3 | (31) | 6 | — | — | 40 |
| *Ae. taeniorhynchus* | 3rd/$T_0$, $T_1$ | Brackish | 2**** | 1 | (14) | 4 | — | — | 31 |
| *Ae. taeniorhynchus* | 2nd/$T_0$, $T_1$ | Brackish | K***** | 7 | (15) | 9 | — | — | 61 |
| *Ae. taeniorhynchus* | 2nd/$T_0$, $T_1$ | Brackish | L***** | 2 | (20) | 4 | — | — | 56 |
| *Ae. taeniorhynchus* | 2nd/$T_0$, $T_1$ | Brackish | M***** | 2 | (20) | 9 | — | — | 61 |
| *An. albimanus* | 2nd/$T_0$, $T_1$ | Fresh | N | 3 | (17) | 5 | — | — | 25 |
| *An. albimanus* | 2nd/$T_0$, $T_1$ | Fresh | O | 1 | (19) | 1 | — | — | 21 |
| *An. albimanus* | 2nd/$T_0$, $T_1$ | Fresh | P | 1 | (19) | 4 | — | — | 24 |
| *An. albimanus* | 2nd/$T_0$, $T_1$ | Fresh | Q | 1 | (19) | 2 | — | — | 22 |

TABLE 10-continued (Example 6). Coating-Regulated Controlled Delivery of Acrobe ® TP or Acrobe ® TP/Dianex ® EC from Powdered or Agglomerated Compositions*

| Mosquito Species | Larval Instar/ Composition Transfer Period (T)** | Water Quality | Composition Code/No. | No. Days to Achieve 100% Larval Control at Composition Transfer Period (No. Days Between Transfers) Test Duration $T_0$ | $(T_0–T_1)$ | $T_1$ | $(T_1–T_2)$ | $T_2$ | (Days)*** |
|---|---|---|---|---|---|---|---|---|---|
| *An. albimanus* | 2nd/$T_0$, $T_1$ | Fresh | R | 1 | (19) | 1 | — | — | 21 |
| *An. albimanus* | 2nd/$T_0$, $T_1$ | Fresh | S | 2 | (18) | 1 | — | — | 21 |
| *An. albimanus* | 2nd/$T_0$, $T_1$ | Fresh | T | 1 | (19) | 1 | — | — | 21 |
| *An. albimanus* | 2nd/$T_0$, $T_1$ | Fresh | U | 1 | (19) | 1 | — | — | 21 |
| *An. albimanus* | 2nd/$T_0$, $T_1$ | Fresh | V | 1 | (19) | 3 | — | — | 23 |
| *An. albimanus* | 2nd/$T_0$, $T_1$ | Fresh | W | 1 | (19) | 1 | — | — | 21 |
| *An. albimanus* | 2nd/$T_0$, $T_1$ | Brackish | N | 3 | (17) | 8 | — | — | 28 |
| *An. albimanus* | 2nd/$T_0$, $T_1$ | Brackish | O | 1 | (19) | 10 | — | — | 30 |
| *An. albimanus* | 2nd/$T_0$, $T_1$ | Brackish | P | 1 | (19) | 15 | — | — | 35 |
| *An. albimanus* | 2nd/$T_0$, $T_1$ | Brackish | Q | 1 | (19) | 6 | — | — | 26 |
| *An. albimanus* | 2nd/$T_0$, $T_1$ | Brackish | R | 1 | (19) | 2 | — | — | 22 |
| *An. albimanas* | 2nd/$T_0$, $T_1$ | Brackish | S | 1 | (19) | 7 | — | — | 27 |
| *An. albimanus* | 2nd/$T_0$, $T_1$ | Brackish | T | 1 | (19) | 1 | — | — | 21 |
| *An. albimanus* | 2nd/$T_0$, $T_1$ | Brackish | U | 10 | (10) | 8 | — | — | 28 |
| *An. albimanus* | 2nd/$T_0$, $T_1$ | Brackish | V | 1 | (19) | 5 | — | — | 25 |
| *An. albimanus* | 2nd/$T_0$, $T_1$ | Brackish | W | 1 | (19) | 2 | — | — | 22 |
| Powdered Compositions - ACROBE ® TP (5% AI Formulation) | | | | | | | | | |
| *Cx. quinquefasciatus* | 2nd/$T_0$, $T_1$ | Fresh | K | 2 | (17) | 7 | (26) | 13 | 65 |
| *Cx. quinquefasciatus* | 2nd/$T_0$, $T_1$ | Fresh | L | 1 | (18) | 14 | (19) | 14 | 66 |
| *Cx. quinquefasciatus* | 2nd/$T_0$, $T_1$ | Fresh | M | 2 | (17) | 5 | (28) | 17 | 69 |
| Powdered Compositions - ACROBE ® TP/DIANEX ® C (5%/10.5% AI 1:1 Formulation) | | | | | | | | | |
| *Ae. taeniorhynchus* | 3rd/$T_1$, $T_2$ | Brackish | E | 4 | (17) | 13 | — | — | 34 |
| Agglomerated Compositions - ACROBE ® TP (5% AI Formulation) | | | | | | | | | |
| *An. albimanus* | 2nd/$T_0$, $T_1$; 1st/$T_2$ | Fresh | A | 2 | (12) | 3 | (21) | 9 | 47 |
| *An. albimanus* | 2nd/$T_0$, $T_1$; 1st/$T_2$ | Fresh | B | 1 | (13) | 3 | (21) | 8 | 46 |
| *An. albimanus* | 2nd/$T_0$, $T_1$; 1st/$T_2$ | Fresh | C | 9 | (05) | 4 | (20) | 7 | 45 |
| *An. albimanus* | 2nd/$T_0$, $T_1$; 1st/$T_2$ | Brackish | A | 2 | (12) | 8 | (16) | 1 | 53 |
| *An. albimanus* | 2nd/$T_0$, $T_1$; 1st/$T_2$ | Brackish | B | 2 | (12) | 3 | (21) | 16 | 54 |
| *An. albimanus* | 2nd/$T_0$, $T_1$; 1st/$T_2$ | Brackish | C | 7 | (07) | 1 | (23) | 18 | 56 |

*Powdered and agglomerated controlled release compositions of Acrobe ® TP or Acrobe ® TP/Dianex ® EC applied at rates of ca. 2.5 and 5.0 lb/acre, respectively.

**$T_0$ = Initial composition introduction; $T_{1,2}$ = No. post-introduction composition transfers.

***Compositions remained in water for test duration as a pretreatment without larvae or during larvae challenges in $T_0$, $T_1$, and $T_2$, and between transfer periods $T_0$–$T_2$ with dead larvae/pupae. Compositions briefly removed with a 100 mesh sieve to transfer formulations from $T_0$, to $T_1$ and $T_1$ to $T_2$ test chambers. Tests terminated even though compositions were still effective in producing 100% control of immatures.

****Powdered compositions initially introduced into water for 12 days without larvae (pretreatment) before being transferred into $T_0$ test chamber with larvae.

*****Powdered compositions initially introduced into water for 30 days without larvae (pretreatment) before being transferred into $T_0$ test chamber with larvae.

EXAMPLE 7

A series of short-term bioassays were conducted in fresh or brackish water against larvae of Anopheles, Aedes, and/or Culex species with controlled release compositions comprising admixtures of the insect growth regulator methoprene (Dianex®EC), the bacteria B.t.i. (Acrobe® TP) or an experimental monomolecular surface film (POE(2) Isostearyl Alcohol), one or more hydrophobic (FK 500 LS, Sipernat® 22S, Wesslon™) and/or hydrophobic (Sipernat® D17) silica or hydrophobic "pin chips" (SeaSweep®) carriers, and one or more cetyl alcohol (specific gravity less than one, insoluble in water), triethyl citrate (Citroflex®2; specific gravity greater than one, soluble in water), tributyl citrate (Citroflex®4; specific gravity greater than one, insoluble in water), and/or n-butyryl tri-n-hexyl citrate (Citroflex® B-6; specific gravity less than one, insoluble in water) coatings, and/ or one or more joint-function polyvinyl alcohol films (specific gravity greater than one, soluble in water) that can act as a coating and carrier. All coatings showed differential surface spreading potentials when applied to the water. Specific formulation components for each of the compositions utilized in these bioassays are presented in Table 11.

Results of larval bioassays against single or mixed species populations indicated that the initial orientation of delivery of an insect growth regulator, bacteria or monomolecular surface film from a controlled delivery composition was dictated by the surface and/or subsurface characteristics of the bioactive agent/coating-encapsulated carrier(s) in an aquatic habitat (Table 12). Changes over time in the initial orientation or direction and rate of delivery in a water column were determined by the specific gravity, solubility, and film-forming characteristics of the coating agent(s) and bioactive agent(s) encapsulated on the carrier(s).

The data indicated that 100% larval control of mixed populations of Anopheles and Culex species occurred in all powdered B.t.i. formulations (2.5 lb/acre application) in 24 hr posttreatment; however, the rates of control within the 24 hr period were observed to be formulation (i.e., coating) dependent. Complete control (i.e., 100%) of larvae of Aedes with two powdered compositions of POE (2) Isostearyl Alcohol (5 lb/acre application) was observed in 11 and 13 days posttreatment while 100% control of larvae of Culex mosquitoes exposed to two "pin chip" compositions of methoprene (2.5 lb/acre application) was observed in 28 and 30 days posttreatment. Mixed populations of Anopheles larvae were killed in both water qualities within 24 hr posttreatment with all polyvinyl alcohol film compositions. These agglomerated admixture formulations (i.e., cubettes) initially floated and differentially solubilized within 24 hr. It appears that air entrapped within the polyvinyl alcohol matrices caused the formulations to float. Cubette agglomeration and hardness were affected by the type of solvent utilized in the fabrication process. Polyvinyl alcohol film(s) and B.t.i. compositions (Codes 12, 13, 14) were secondarily admixed with 0.15–0.5 g soluble starch, Carboset®514H, Carbopol® ETD 2001, Narlex®D-82, Versa® TL-502, Citroflex® A-2, Morflex® 150, FK 500 LS, Sipernat® D17, ethoxylated alcohols, and/or salts (e.g., NaCl Instant Ocean®). Additions of one or more binder, coating agents, carriers, and/or additional ingredients to the formulations indicated in Codes 12, 13, 14 were observed to significantly affect component dissociation from the cubettes as well as the surface/subsurface orientation of the cubettes/cubette components in the water column. The type of salt(s) utilized in the aqueous formulation and the type of solvent(s) utilized in the aqueous agglomeration and drying protocols were observed to have a significant affect on the agglomeration performance and rigidity of the matrices containing the additional admixture ingredients.

TABLE 11

(Example 7).
Formulation Components in Powdered, Chipped or Agglomerated Controlled Delivery Compositions

| Composition No. | Concentration of Admixtures in Powdered and Chipped Compositions |
|---|---|
| | Powdered Compositions* |
| 5 | 10 g B.t.i.(Acrobe ®TP) + 20 g cetyl alcohol + 85 g hydrophobic silica (Sipernat ®D17) + 85 g hydrophilic silica (Wesslon ™) |
| 6 | 10 g B.t.i. (Acrobe ®TP) + 10 g cetyl alcohol + 10 g triethyl citrate (Citroflex ®2) + 85 g hydrophobic silica (Sipernat ®D17) and 85 g hydrophilic silica (Wesslon ™) |
| 7 | 10 g B.t.i. (Acrobe ®TP) + 10 g cetyl alcohol + 10 g n-buty-rltri-n-hexyl citrate (Citroflex ®B-6) + 85 g hydrophobic silica (Sipernat ®D17) + 85 g hydrophilic silica (Wesslon ™) |
| 8 | 24.75 g Monomolecular Surface Film (POE(2) Isostearyl Alcohol) + 0.25 g triethyl citrate (Citroflex ®2) + 75 g hydrophilic silica (Sipernat ®22S) |
| 9 | 24.75 g Monomolecular Surface Film (POE(2) Isostearyl Alcohol) + 0.25 g tributyl citrate (Citroflex ®4) + 75 g hydrophilic silica (Sipernat ®22S) |
| | Chipped Compositions** |
| 10 | 5 g methoprene (Dianex ®EC) + 5 g triethyl citrate (Citroflex ®2) + 90 g "pin chips" (SeaSweep ®) |
| 11 | 5 g methoprene (Dianex ®EC) + 5 g n-butyrltri-n-hexyl citrate (Citroflex ®B-6) + 90 g "pin chips" (Seasweep ®) |
| | Agglomerated Compositions*** |
| 12 | 3 g B.t.i. (Acrobe ® Biolarvicide) + 12 g polyvinyl alcohol film (MonoSol ® 8000 series) + 45 g distilled water + acetone, methyl ethyl ketone or 2-propanol bath series |
| 13 | 3 g B.t.i. (Acrobe ® Biolarvicide) + 12 g polyvinyl alcohol film (MonoSol ® 7000 series) + 45 g distilled water + acetone, methyl ethyl ketone or 2-propanol bath series |
| 14 | 3 g B.t.i. (Acrobe ® Biolarvicide) + 6 g polyvinyl alcohol film (MonoSol ® 8000 series) + 6 g polyvinyl alcohol film (MonoSol ® 7000 series) + 45 g distilled water + acetone, methyl ethyl ketone or 2-propanol bath series |

*Cetyl alcohol (heated to 60° C.), triethyl citrate, tributyl citrate, and/or n-butyrltri-n-hexyl citrate was added to 600 g acetone and mixed for ca. 5 minutes (speed #6, wire whip) with a KitchenAid ® KSM 90 hand mixer in a 4 1/2 qt stainless steel bowl. B.t.i. or the experimental monomolecular surface film was slowly added to the solvent-base formulations of coatings while mixing (stir, speed #6, wire whip) was continued for ca. 5 minutes. Hydrophobic and/or hydrophilic silica was added to each solvent-base bioactive agent/coating formulation while mixing (stir, speed #6, wire whip, flat beater blade) was continued for ca. 3 hr to drive off the acetone and as sure that each silica was uniformly encapsulated with the homogeneous mixture of each bioactive agent and coating(s). Each powdered composition was placed in a low humidity room (ca. 27–38% RH) for ca. 3 to 4 hr to assure volatilization of the solvent. The dry powdered compositions were stored in zip-lock bags or glass bottles until being utilized in mosquito bioassays.

**Triethyl citrate or n-butyrltri-n-hexyl citrate and methoprene were added to 300 g acetone in 1000 ml Nalgene bottles and placed on a paint shaker (Miller Strokemaster ™) for ca. 1 hr to assure that the insect growth regulator formulation was well mixed "Pin chips" (ca. 2 × 8 mm) were added to the bottles containing the acetone/methoprene/citrate formulations and hand shaken for ca. 10–30 seconds to assure that the "pin chips" were saturated with the formulations. "Pin chips" continued to soak in the formulations for ca. 18 hr before being removed on sieves and placed in a drying room (ca. 27–38% RH) for ca. 24 hr to assure volatilization of the acetone. The dry "pin chip" formulations were placed into zip-lock bags until being used for mosquito bioassays.

***One or more polyvinyl alcohol films were dissolved in distilled water in a plastic beaker. B.t.i. was mixed with the aqueous formulation of joint-function coating/carrier with a KitchenAid ® KSM 90 hand mixer for ca. 1 to 2 minutes. The insecticide formulations were poured into 2 ounce glass medicine bottles and vigorously shaken by hand for ca. 1 minute. 7–10 g water-base polyvinyl alcohol films/B.t.i. formulations were added to plastic centrifuge tubes (ca. 60 ml capacity) containing ca. 35–40 g acetone, methyl ethyl ketone or 2 propanol. The centrifuge tube was capped and vigorously hand shaken to solidify to polyvinyl alcohol film(s) and B.t.i. admixtures into a unified mass within the aqueous-acetone, aqueous-methyl ethyl ketone or aqueous-2- propanol medium. The solid mass from each tube was removed and placed into 50 ml glass beakers containing ca. 40 g acetone, methyl ethyl ketone or 2-propanol for a series of five one minute washes to remove entrapped water from the solid matrix. The solid mass was removed from each acetone, methyl ethyl ketone or 2-propanol bath and thoroughly air-dried in a low humidity room (ca. 27–38% RH) for ca. 72 hr. The solid compositions were stored in zip-lock bags or glass bottles until being used for mosquito bioassays. Remaining stock formulations of water, polyvinyl alcohol film(s), and B.t.i. were stored in a refrigerator (ca. 40° F.) for future use.

TABLE 12

(Example 7). Coating-Regulated Delivery of Acrobe ® TP, Dianex ® EC or POE(2) Isostearyl Alcohol from Powdered, Chipped or Agglomerated Compositions

| Mosquito Species | Larval Instar | Water Quality | Composition No. | No. Days to Achieve 100% Control of Larvae, Pupae and/or Emerging Adults |
|---|---|---|---|---|
| Powdered Composition - Acrobe ®TP (5% AI Formulation)* | | | | |
| *An. albimanus*/ *Cx. quinquefasciatus* | 2nd/ 2nd | Fresh | 5 | 1 |
| *An. albimanus*/ *Cx. quinquefasciatus* | 2nd/ 2nd | Fresh | 6 | 1 |

TABLE 12-continued (Example 7). Coating-Regulated Delivery of Acrobe ® TP, Dianex ® EC or POE(2) Isostearyl Alcohol from Powdered, Chipped or Agglomerated Compositions

| Mosquito Species | Larval Instar | Water Quality | Composition No. | No. Days to Achieve 100% Control of Larvae, Pupae and/or Emerging Adults |
|---|---|---|---|---|
| *An. albimanus*/ *Cx. quinquefasciatus* | 2nd/ 2nd | Fresh | 7 | 1 |
| *An. albimanus*/ *Cx. quinquefasciatus* | 2nd/ 2nd | Brackish | 5 | 1 |
| *An. albimanus*/ *Cx. quinquefasciatus* | 2nd/ 2nd | Brackish | 6 | 1 |
| *An. albimanus*/ *Cx. quinquefasciatus* | 2nd/ 2nd | Brackish | 7 | 1 |
| Powdered Compositions - POE(2) Isostearyl Alcohol (25% AI Formulation)** | | | | |
| *Ae. taeniorhynchus* | 3rd | Brackish | 8 | 11 |
| *Ae. taeniorhynchus* | 3rd | Brackish | 9 | 13 |
| Chipped Compositions - Dianex ® EC (5% AI Formulation)*** | | | | |
| *Cx. quinquefasciatus* | 2nd | Fresh | 10 | 26 |
| *Cx. quinquefasciatus* | 2nd | Fresh | 11 | 23 |
| Agglomerated Compositions - Acrobe ® TP (20% AI Formulation)**** | | | | |
| *An. albimanus* | 2nd | Fresh | 12 | 1 |
| *An. albimanus* | 2nd | Fresh | 13 | 1 |
| *An. albimanus* | 2nd | Fresh | 14 | 1 |
| *An. albimanus* | 2nd | Brackish | 12 | 1 |
| *An. albimanus* | 2nd | Brackish | 13 | 1 |
| *An. albimanus* | 2nd | Brackish | 14 | 1 |

*Powdered controlled delivery compositions of B.t.i. one or more cetyl alcohol and/or citrate coatings, and one or more hydrophobic and/or hydrophilic silica carriers were applied at a rate of ca. 2.5 lb/acre (i.e., 0.005 g,bioassay test chamber).

**Powdered controlled delivery compositions of a monomolecular surface film, a citrate coating, and a hydrophilic silica carrier were applied at a rate of ca. 5 lb/acre (i.e., 0.01 g/bioassay test chamber).

***Chipped controlled delivery compositions of methoprene, a citrate coating, and a hydrophobic "pin chip" carrier were applied at a rate of ca. 2.5 lb/acre (i.e., 5 "pin chips"; 0.005 g/bioassay test chamber).

****Agglomerated controlled delivery compositions (i.e., cubettes) of B.t.i. (20%) and a water and solvent-free joint-function polyvinyl alcohol film coating/carrier (80%) were applied at a rate of ca. 5 lb/acre (i.e., one, 0.01 g cubette/bioassay test chamber). Aqueous insecticide formulations fabricated into solid mass by a series of solvent precipitation and evaporation procedures.

EXAMPLE 8

In another evaluation, 0.01, 0.05, and 0.1 g Pemulen® TR-1 or Pemulen® TR-2 acrylic copolymer suspending agents were added to 47.5 g distilled water in 50 ml glass medicine bottles and vigorously shaken by hand for ca. 2–3 minutes to form a homogeneous mixture. 2.5 g of the powdered controlled release compositions of B.t.i. (Acrobe® TP), one or more hydrophobic and/or hydrophilic silica carriers and one or more Citroflex®, Morflex® and/or cetyl alcohol coatings (Examples 1–7) were added to each of the aqueous acrylic copolymer formulations and placed on a mechanical shaker and vigorously mixed for ca. 5 minutes to assure that the silica-base compositions were uniformly suspended throughout the water column. Results of the suspendability tests indicated that these powdered compositions could be readily dispensed in water with conventional spray equipment. Suspension of compositions in petroleum or nonpetroleum oils for spray application is also proposed.

EXAMPLE 9

In another test, an aqueous formulation of the aquatic herbicide Aquathol®K (dipotassium salt of endothall) was admixed with a joint-function (carrier/coating) polyvinyl alcohol film (MonoSol® 8000 series, M-7030, M-8533 or M-8030) and agglomerated into a solidified controlled delivery mass in a series of solvent precipitation and evaporation procedures. The admixing protocol utilized was similar to procedures described in Examples 4, 5, and 7. As indicated in the earlier examples, polyvinyl alcohol film (specific gravity greater than one) is soluble in water (temperature dependent) but insoluble in most organic and inorganic solvents, hydrocarbons or oils. These properties are also similar for polyethylene oxide and hydroxypropyl methyl cellulose water-soluble films. MonoSol® 8000 series was obtained from the manufacturer as solid sheets/pouches and dissolved in water (20% polyvinyl alcohol film) while MonoSol® M-7030, M-8533 and M-8030 were obtained as water-base solutions (16.1–16.4% polyvinyl alcohol film).

The following formulations were utilized in fabricating the joint-function polyvinyl alcohol compositions of Aquathol®K: Composition AK1–4 g dipotassium salt of endothall (Aquathol®K)+12.5 g polyvinyl alcohol film (MonoSol® 8000 series)+46 g distilled water+acetone bath series; Composition AK2–2. g to dipotassium salt of endothall (Aquathol®K)+7.4 g polyvinyl alcohol film (MonoSol® M-7030)+40.6 g distilled water+acetone bath series; Composition AK3–2 g dipotassium salt of endothall (Aquathol®K)+7.3 g polyvinyl alcohol film (MonoSol® M-8533)+40.7 distilled water+acetone bath series; and Composition AK4–2 g dipotassium salt of endothall (Aquathol®K)+7.3 g polyvinyl alcohol film (MonoSol® M-8030)+40.7 g distilled water+acetone bath series.

The dried agglomerated briquet compositions of AK1, AK2, AK3, and AK4 consisted of 24.4, 21.5, 21.7, and 21.8% (w/w) dipotassium salt of endothall, respectively. Commercial Aquathol®K granules contain only 10.1% dipotassium salt of endothall.

Results of the admixing procedures indicated that high levels of Aquathol®K can be agglomerated into solid polyvinyl alcohol-base compositions for fast-release application into an aquatic habitat for control of nuisance vegetation. All compositions solubilized in fresh water within 2 hr of introduction and showed differential degrees of floating or sinking depending on the type and/or concentration of polyvinyl alcohol utilized in the formulation.

Loading levels were significantly higher than the standard commercially available granular Aquathol®K product (i.e., 10.1% dipotassium salt of endothall), and therefore, a lesser amount (on a weight basis) per acre of MonoSol®/Aquathol®K would be required to treat an acre of aquatic weeds when compared to the amount or weight of conventional Aquathol®K granular product needed per acre to be equivalent to the concentration of dipotassium salt of endothall in the composition. The results indicated that significantly higher loading levels can be obtained with the polyvinyl alcohol-base protocol. Addition of one or more coatings, surfactants, binders, and the like is expected to change the controlled release profiles of the compositions. Any herbicide can be fabricated into a solid controlled delivery composition utilizing the joint-function polyvinyl alcohol-base admixing protocol.

EXAMPLE 10

In this example, aqueous formulations of the insect growth regulator pyriproxyfen (Nylar® 10% EC) was admixed with a gum/molasses-base bait and a joint-function (carrier/coating) polyvinyl alcohol film (MonoSol® 8000 series) and agglomerated into three types of unified solid masses (i.e., sheets, coatings, and extrusions). The admixing and fabrication procedures are described in Table 13. In this example, the agglomerated joint-function controlled delivery compositions of matter are utilized to illustrate the present invention, and were designed to target (i.e., control) a terrestrial pest. Nymphs (7–10 mm) of the German cockroach *Blattella germanica* (Navy 3 strain) were used as models to demonstrate the efficacy of the agglomerated controlled delivery insecticide-bait compositions in a terrestrial environment.

A series of long-term transfer bioassays (Table 14) were conducted in grey polyethylene trays (ca. 51×31×15 cm; Consolidated Plastics, Twinsburg, Ohio). An extruded chamber, a section (85 mm diameter) of poured sheet, or a coated vial was placed in one corner of a tray. The extruded chamber or small section of the poured sheets was placed in a 35×10 mm plastic petri dish. One 35×10 mm plastic petri dish containing ca. 5.0 g rabbit chow was placed in the opposite corner as an alternate food source. A cotton-plugged glass vial (40 ml) containing water was placed in a 100×15 mm square petri dish and positioned in the center of the tray. The top edge of each test container was treated with a border of petroleum jelly and mineral oil mix to prevent escape of the cockroaches. Twenty-five nymphs of the German cockroach were added to each tray. Tests were replicated three times with each joint-function composition.

The effects of the Nylar® (i.e., twisted wing and dark pigmentation sterility indices) on the cockroaches were recorded at 24 hr posttreatment intervals. Nylar® effected cockroaches were removed at each observation period. When 100% of the cockroaches showed growth regulator effects, each bait-insecticide chamber, sheet or vial was transferred to a new test tray containing new cockroach nymphs, water, and rabbit chow. Tests were terminated if control mortality exceeded 10% or if any normal adult cockroaches were observed after being exposed to the Nylar/bait/polyvinyl alcohol controlled delivery compositions as nymphs. Tests were conducted in a room maintained at ca. 27° C. and 61–80% RH.

It should be noted that similar joint-function controlled delivery compositions of 0.5% Dursban® 4-E, gum-molasses-bait and polyvinyl alcohol showed comparable efficacy against adult (12–14 mm) German cockroaches. These bait-insecticide compositions are also expected to be effective against certain species of ants that are attracted to baits.

It is apparent from these terrestrial tests as well as tests performed in an aquatic environment that a variety of single and joint-action coating-regulated controlled delivery composition and devices of the present invention can be effective in releasing a variety of bioactive agents (e.g., pesticides) in both aquatic and terrestrial environments for prolonged periods.

TABLE 13

(Example 10).
Formulation Components in Agglomerated Joint-Function Controlled Delivery Compositions

| Composition Code | Concentration of Admixtures in Agglomerated Joint-Function Compositions |
|---|---|
| | Extruded Chamber Compositions* |
| E1 | 2.0 g pyripoxyfen (Nylar ® 10% EC) + 39.6 g polyvinyl alcohol film (MonoSol ® 8000 series) + 0.2 g gum/molasses-base bait + 158.2 g distilled water. |
| | Poured Sheet Compositions** |
| S1 | 2.0 g pyripoxyfen (Nylar ® 10% EC) + 39.6 g polyvinyl alcohol film (MonoSol ® 8000 series) + 0.2 g gum/molasses-base bait + 158.2 g distilled water. |
| | Coated Vial Compositions*** |
| V1 | 2.0 g pyripoxyfen (Nylar ® 10% EC) + 39.6 polyvinyl alcohol film (MonoSol ® 8000 series) + 0.2 g gum/molasses-base bait + 158.2 g distilled water. |

*Polyvinyl alcohol film (2 mil) was dissolved in distilled water in a plastic beaker. Pyriproxyfen the bait composition were mixed with the aqueous formulation of joint-function coating/carrier in a 1/2 gal plastic beaker by hand-stirring with a spatula for ca. 15 min or by mixing the formulation with a KitchenAid ® KSM 90 in a stainless steel bowl for ca. 2–5 min (speed #6; wire whip). A series of ca. 9.0 g aliquots of the homogeneously mixed aqueous insecticide-bait formulation was poured into plastic Peel-A-Way ® tissue embedding molds (2 × 2 × 2 cm). Molds were placed in a curing/drying room maintained at ca. 25–26° C. and 27–38% RH for ca. 10 days to allow slow drying and adhesion of the semiviscous insecticide-bait to the wails of the embedding molds to cause self-extrusion of the insecticide-bait formulation to form an open central pocket or hollow core in each mold. The resultant self-extruded, joint-function insecticide-bait chambers were ca the same size and shape as the molds from which they were removed. Each insecticide-bait chamber was open at one end, and was ca. 2 mm in thickness at the bottom and ca. 0.5 mm on each side of the hollow central core. The dry self-extruded insecticide-bait chamber compositions were stored in zip-lock bags until being used in cockroach bioassays.

** Polyvinyl alcohol film (2 mil) was dissolved in distilled water in a plastic beaker. Pyriproxyfen and the bait composition were mixed with the aqueous formulation of joint-function coating-carrier in a 1/2 gal plastic beaker by hand-stirring with a spatula for ca. 15 min or by mixing the formulation with a KitchenAid ® 90 KSM mixer in a stainless steel bowl for 2–5 min (speed #6; wire whip). A thin film of the aqueous joint-function insecticide-bait composition was poured over the bottom of several Pyrex ® 3 quart pans (33 × 23 × 5 cm). The glass pans were placed in a curing/drying room maintained at ca. 25–26° C. and 27–38% RH for ca. 48 hr. The dry transparent polyvinyl alcohol/bait/Nylar ® 10% EC films (ca. 0.1 mm in thickness) were peeled off the bottom of the glass pans in a continuous sheet, placed on aluminum foil, and stored in zip-lock bags until being used in cockroach bioassays.

***Polyvinyl alcohol film (2 mil) was dissolved in distilled water in a plastic beaker. Pyripoxyfen and the bait composition were mixed with the aqueous formulation of joint-function carrier-coating in a 1/2 gal plastic beaker by hand-stirring with a spatula for ca. 15 min or by mixing the formulation with a KitchenAid ® KSM 90 mixer in a stainless steel bowl for 2–5 min (speed #6; wire whip). A thin film of the semiviscous insecticide-bait joint-action formulation was deposited on the walls of a series of 2 dram screw cap vials (DSA2-10458; Owens-Illinois Glass Co., Toledo, Ohio), by filling each vial to the top with the homogeneous formulation, and then rapidly pouring the formulation back out. The vials were inverted over a screen tray and allowed to drain the excess formulation for ca. 2 hr. The open vials were placed in a curing/drying room maintained at ca. 25–26° and 27–38% RH for ca. 24 hr. Vials coated with the dry polyvinyl alcohol/bait/Nylar ® 10% EC film were capped and stored in zip-lock bags until being used in cockroach bioassays.

TABLE 14

(Example 10). Coating-Regulated Controlled Delivery of Nylar ® EC from Agglomerated Joint-function Compositions

| Cockroach Species | Nymph Size (mm)/ Composition Transfer Test Duration Period (T)* (Days)** | Composition Code | No. Days to Achieve 100% Nymphal Growth Regulator Effects at Composition Transfer Period (No. Days Between Transfers) $T_0$ | $(T_0 \rightarrow T_1)$ | $T_1$ | Test Duration |
|---|---|---|---|---|---|---|
| Extruded Chamber Compositions - NYLAR ® 10% EC (0.5% AI Formulation)*** | | | | | | |
| *Blattella germanica* | 7–10/$T_0$, $T_1$ | E1 | 39 | 2 | 50 | 91 |
| Poured Sheet Compositions - NYLAR ® 10% EC (0.5% AI Formulation)**** | | | | | | |
| *Blattella germanica* | 7–10/$T_0$, $T_1$ | S1 | 34 | 2 | 48 | 84 |
| Coated Vial Compositions - NYLAR ® 10% EC (0.5% AI Formulation)***** | | | | | | |
| *Blattella germanica* | 7–10/$T_0$, $T_1$ | VI | 35 | 2 | 60 | 96 |

*$T_0$ = Initial Composition Introduction; $T_1$ = No. post-introduction transfers.
**Compositions remained in test chambers until all replicates showed Nylar ®-induced growth regulator effects (i.e., twisted wing/dark pigment abnormalities) in all cockroach nymphs. Compositions were allowed to remain in test chambers for an additional 2-day period ($T_0 \rightarrow T_1$) before being transferred to a new test chamber containing new nymphs and food. All tests were terminated at indicated time period even though all joint-function compositions were still effective in producing 100% growth regulator effects (= 100% control) in cockroach nymphs.
***Average extruded chamber composition weight = ca. 1.48 g./chamber.
****Average poured sheet composition weight = ca. 0.28 g/sheet.
*****Average coating weight in coated vial compositions = ca. .06 g/vial.

EXAMPLE 11

Biodegradable 12/20 mesh cellulose complex granules (Biodac®) and 10/14 mesh corn cob granules were selected as matrices for use in the controlled delivery system in this study. These carriers are widely used in agrochemical operations for delivery of a variety of aquatic and terrestrial pesticides.

A series of nontoxic and biodegradable or erodible coating complexes consisting of a blend of two coatings were formulated with one of the granular carriers and a *Bacillus thuringiensis* var. *israelensis* (BTI) formulation labeled Vetobac® Technical Powder (5000 ITU/mg) or Bactimos® Primary Powder (7000 ITU/mg), or a methoprene formulation labeled Dianex® Emulsifiable Concentrate (32.8% S-methoprene). The compositions were formulated for prolonged subsurface delivery to target *Aedes taeniorhynchus* larvae in 10%, 50% or 100% artificial sea water (Instant Ocean®) or *Culex quinquefasciatus* in well water purified by reverse osmosis filtration (RO). The preflood or pretreatment potential of the granules was also evaluated.

A series of stress test granule-transfer bioassays was designed to simulate pretreatment of flooded semipermanent brackish water habitats that initially have no larval breeding and direct treatment of multiple broods of mosquito larvae in permanent fresh water or semipermanent brackish/salt water habitats that periodically flood and dry. Bioassay protocol consisted of challenging the Aedes or Culex species with the granules composed of Biodac® or corn cobs, a coating complex, and a BTI or methoprene formulation for ca. 90–100 days (Table 15).

TABLE 15[(1)]

| | |
|---|---|
| Type I = | 92.3% Biodac ® + 3.8% Coating Complex A/B + 3.9% Vectobac ®TP |
| Type II = | 97.6% Biodac ® + 1.2% Coating Complex C/E + 1.2% Dianex ®EC |
| Type III = | 90.4% corn cob + 4.8% Coating Complex A/D + 4.8% Vectobac ®TP |
| Type IV = | 90.4% corn cob + 4.8% Coating Complex A/B + 4.8% Bactimos ®PP |

[(1)]A/B 1:1 wt. basis formulated as follows:
5 wt. % active agent
5 wt. % coating
90 wt. % carrier
Ratio of components in final product reported in Table 15
A = Triethyl citrate
B = n-Butyryltri-n-hexyl citrate
C = Cetyl alcohol
D = Tri-n-butyl citrate
E = Dicyclohexyl phthalate Bioassays were conducted in ½ gal plastic cups containing 1000 ml of RO, 10%, 50%, or 100% artificial sea water (Instant Ocean®) and ten 2nd or 3rd instar *Ae. taeniorhynchus* or *Cx. quinquefasciatus* larvae (i.e., 10 larvae=1 brood). Application rates of 4 corn cob-base or 6 Biodac® base granules/cup were equivalent to ca. 5 lbs/acre. Tests were replicated 3 times.

Percent mortality was recorded at 24 hr. posttreatment intervals. The granules were transferred to new cups containing new larvae at intervals that were dependent on the time required to achieve 100% mortality of a larval brood in a particular water quality. The coating complex, bioactive agent, and matrix integrities were stressed throughout a granule-transfer bioassay by an intermittent series of washings, wettings, and drying cycles. A test was terminated before the 90–100 day test period if a composition did not kill 100% of a larval brood or if mortality in control cups exceeded 10%. Larvae were fed ground rabbit chow throughout a test series. Tests were conducted in a room maintained at ca. 27° C.

Results and Discussion

Results of granule-transfer bioassays against *Ae. taeniorhynchus* (A.T.) and *Cx. quinquefasciatus* (C.Q.) are presented in Table 16. Controlled delivery of BTI from Type I, III, and IV granular compositons was observed to follow first order or square-root-of-time kinetics while methoprene release from Type II granular compositions follow "pseudo"

zero-order kinetics. Prolonged mosquito control was related to the type of coating complex utilized in a formulation.

TABLE 16

Efficacy of Granules Against Mosquito Larvae

| Granule Type | Habitat* (Pre, Semi, Perm) | Species | No. Breeds Controlled | Control Duration (Days) |
|---|---|---|---|---|
| I | Pre | A.T. | 6 | 105 |
| I | Semi | A.T. | 7 | 98 |
| I | Perm | C.Q. | 7 | 105 |
| II | Pre | A.T. | 3 | 90 |
| II | Semi | A.T. | 4 | 94 |
| II | Perm | C.Q. | 4 | 97 |
| III | Pre | A.T. | 6 | 104 |
| III | Semi | A.T. | 6 | 107 |
| III | Perm | C.Q. | 7 | 108 |
| IV | Pre | A.T. | 6 | 109 |
| IV | Semi | A.T. | 7 | 98 |
| IV | Perm | C.Q. | 6 | 90 |

*Pre = Pretreated semipermanent habitat (flood/dry cycles - no initial larvae); Semi = Direct treatment semipermanent habitat (flood/dry cycles - initial larvae); Perm = Permanent water habitat (Flood cycles only - initial larvae).

The foregoing coating components, bioactive agents and carrier components can be selected to control or eliminate various terrestrial organisms, and especially nuisance plant and animal organisms such as weeds, rodents, insects, and mites, including but not limited to cockroaches, ants, fire ants, termites, and other varieties of biting insects, disease carrying insects, parasites and pathogens, crop eating insects, parasites and pathogens and wood eating insects. The coatings that are selected in this regard are the degradable ones, e.g. biodegradable coatings selected from those listed above, and those that also will protect the bioactive agent from degradation, especially ultraviolet light degradation. The coatings are also selected to release the bioactive agent over a period of time so as to increase the effectiveness of the bioactive agent.

The compositions of the invention can also be utilized in the treatment of parasitic or insect caused diseases in animals, especially the G.I. tract of animals such as ruminants, by selecting those components of the composition that are approved for animal use. When properly administered they can be employed to provide time release compositions for the treatment of various diseases and disorders. Non-bioactive compounds or compositions can be used in lieu of the bioactive agents for the treatment of certain disorders such as the treatment of hoven in ruminants by means of surfactant silicone compounds. Some non-limiting examples of other compounds that may be used in the treatment of animals is disclosed by Drummond et al., *Control of Arthropod Pests of Livestock: A Review of Technology,* 1988, CRC Press, Inc. which is incorporated herein by reference.

A variety of medicaments or pharmaceuticals can also be incorporated into the time release compositions as trans-dermal patches or implants for treatments of disorders or diseases in man and animals.

In the course of preparing the various compositions of the invention it was further discovered that in many instances the materials employed as coatings, carriers, and binders were interchangeable. Joint-function carrier coating materials have been described, but in the broader aspects of the invention, the coating, carrier, and binder compounds or compositions are to be categorized primarily by the way they are employed in the composition i.e. by the way the function because of the interchangeability of the various compounds and compositions that are usable in this regard.

In a further embodiment, the invention comprises a composition of matter comprising a controlled delivery system for one or more fragrance, flavorant or food additive which includes at least one fragrance, flavorant, or food additive and a coating component for regulating the controlled release rate and release profile of the fragrance, flavorant, or food additive or combination of fragrance, flavorant, or food additive especially the 2, 3 or 4 component combinations of each or with one another. Applicant has previously defined release rate and release profile.

This composition of matter in a further embodiment also includes a carrier component which the applicant previously defined herein. Additionally, the applicant employs joint-function carrier/coating agents as defined herein in the foregoing fragrance composition of matter. Especially suitable coating components comprise the high molecular weight organic plasticizer materials also as defined previously herein.

The invention also includes a method of controlling the delivery of a fragrance material by employing the aforesaid fragrance composition of matter on a carrier or a substrate, such as paper, building materials, or any surface which a user desires to make more attractive by the emission of a pleasant fragrance or undesirable by means of a repelling fragrance.

Fragrance materials are further defined and listed in *The Fragrance Foundation Reference Guide,* 1992/1993, and subsequent editions, all published by the Fragrance Foundation, 145 East 32nd Street, New York, N.Y. 10016-6002, listing over 1100 fragrances which applicant incorporates herein by reference.

Repelling fragrances include by way of example mercaptans and 4–6 carbon atom aliphatic organic acids all of which are described in Kirk-Othmer, *Encyclopedia of Chemical Technology,* 1st, 2nd, 3rd and 4th Editions incorporated herein by reference. These fragrances find use in keeping pests from certain areas and also in military applications to deny territory to hostile forces.

Compositions of matter in further embodiments comprise controlled delivery systems for one or more flavors, food additives or nutrients, as well as other non-pesticidal bioactive agents.

Carrier and coatings for flavorants, and food additives comprise those listed herein and their equivalents that have FDA approval. Packaging non-ingestible carriers in FDA approved porous materials such as tea bags, sanitized fabric enclosures and the like allows their use in applications where delivery of the flavorant or food additive takes place by fluid (gas or liquid) extraction from the package.

The invention also comprises a method for delivering a flavorant or food additive by means of the coating optionally in combination with the carrier both described herein.

Risch et al. *ACS Symposium Series* 590, *Encapsulation and Controlled Release of Food Ingredients* American Chemical Society 1995 incorporated herein by reference describes flavorants and food additives.

The principles, preferred embodiments, and modes of operation of the present invention have been described in the foregoing specification. The invention which is intended to be protected here, however, is not to be construed as limited to the particular forms disclosed, since these are to be regarded as illustrative rather than restrictive. Variations and changes may be made by those skilled in the art without departing from the spirit of the invention.

What is claimed is:

1. An article of manufacture consisting essentially of a porous, degradable or soluble container having therein a composition of matter consisting essentially of a complex for treating a population of one or more aquatic organisms in a column of water, said complex consisting essentially of at least one controlled delivery system wherein said controlled delivery system consists essentially of an admixture of at least one carrier component, at least one bioactive agent as a component selected for treating a population of one or more aquatic organisms and at least one organic plasticizer coating component for regulating the controlled release rate and release profile of said bioactive agent, said components being selected to sink or float so that said complex will permeate and remain in any planar or volumetric segment of a water column for a period of time sufficient to effectively treat a population of one or more aquatic organisms wherein said carrier consists essentially of from about 50% to about 99% by weight of silicas, cellulose fibers, metal oxides, clays, infusorial earth, slag, lava, paper, hydrophobic wood pin chips, vermiculite, cork, corn cobs, bagasse, seeds, seed hulls, carbon materials, starches, modified starches, carrageenan, algin, xanthates, agar, fluorinated polymeric materials, plaster, gypsum, cement, concrete, asphalt, wood, fiber glass, glass, metals, metal alloys, clothing fabrics, mineral aggregate, leather, natural fibers, synthetic fibers, liposomes, lipospheres, or food proteins and combinations thereof, an optional joint-function carrier/coating which is a polyvinyl alcohol polymer, polyethylene oxide, hydroxpropyl methyl cellulose, cetyl alcohol, stearyl alcohol, and combinations thereof where said bioactive agent is present in an amount from about 0.0001% to about 50% by weight and are insecticides, toxicants, monomolecular surface films, petroleum oils, insect growth regulators, plant growth regulators, animal growth regulators, microbial control agents, medicaments, antibiotics, pathogens, parasites, bactericides, viricides, fungicides, algaecides, herbicides, nematicides, amoebicides, miticides, acaricides, predicides, schistisomicides, molluscicides, larvicides, pupicides, ovicides, adulticides, nymphicides, attractants, repellents, growth stimulants, feeding stimulants, nutrients, hormones, chemosterilants, pheromones, fragrances, flavorants, food additives and combinations thereof, from about 1.0% to about 50% by weight of said organic plasticizer coating component wherein said organic plasticizer is water soluble or biodegradable or erodible, for regulating the controlled release rate and release profile of said bioactive agent where said plasticizer is acetate, adipate, azeleate, benzoate, caprylamide, capramide, caprate, citrate, cocoate, fumarate, glutarate, glycolate, heptanoate, isobutyrate, isophthalate, laurate, linoleate, maleate, mellitate, myristate, octanoate, oleate, palmitate, pelargonate, phosphate, phthalate, ricinoleate, sebacate, stearate, succinate, toluate, tallate, decanoate, or epoxidized vegetable oils, a toluamide or chlorinated paraffins, for regulating the controlled release rate and release profile of said bioactive agent, said components being selected so that said complex will remain in an application site for a period of time sufficient to effectively treat a population of one or more terrestrial organisms, and wherein said composition is free of superabsorbent polymers.

2. An article of manufacture consisting essentially of a container with at least one dispensing aperture, said container having therein a composition of matter consisting essentially of a complex for treating a population of one or more aquatic organisms in a column of water, said complex consisting essentially of at least one controlled delivery system wherein said controlled delivery system consists essentially of an admixture of at least one carrier component, at least one bioactive agent as a component selected for treating a population of one or more aquatic organisms, and at least one organic plasticizer coating component for regulating the controlled release rate and release profile of said bioactive agent, said components being selected to sink or float so that said complex will permeate and remain in any planar or volumetric segment of a water column for a period of time sufficient to effectively treat a population of one or more aquatic organisms, wherein said carrier consists essentially of from about 50% to about 99% by weight of silicas, cellulose fibers, metal oxides, clays, infusorial earth, slag, lava, paper, hydrophobic wood pin chips, vermiculite, cork, corn cobs, bagasse, seeds, seed hulls, carbon materials, starches, modified starches, carrageenan, algin, xanthates, agar, fluorinated polymeric materials, plaster, gypsum, cement, concrete, asphalt, wood, fiber glass, glass, metals, metal alloys, clothing fabrics, mineral aggregate, leather, natural fibers, synthetic fibers, liposomes, lipospheres, or food proteins and combinations thereof, an optional joint-function carrier/coating which is a polyvinyl alcohol polymer, polyethylene oxide, hydroxpropyl methyl cellulose, cetyl alcohol, stearyl alcohol, and combinations thereof where said bioactive agent is present in an amount from 0.0001% to about 50% by weight and are insecticides, toxicants, monomolecular surface films, petroleum oils, insect growth regulators, plant growth regulators, animal growth regulators, microbial control agents, medicaments, antibiotics, pathogens, parasites, bactericides, viricides, fungicides, algaecides, herbicides, nematicides, amoebicides, miticides, acaricides, predicides, schistisomicides, molluscicides, larvicides, pupicides, ovicides, adulticides, nymphicides, attractants, repellents, growth stimulants, feeding stimulants, nutrients, hormones, chemosterilants, or pheromones, fragrances, flavorants, food additives and combinations thereof, said organic plasticizer coating component being present in an amount from about 1.0% to about 50% by weight wherein said organic plasticizer is water soluble or biodegradable or erodible, for regulating the controlled release rate and release profile of said bioactive agent where said plasticizer is an acetate, adipate, azeleate, benzoate, caprylamide, capramide, caprate, citrate, cocoate, fumarate, glutarate, glycolate, heptanoate, isobutyrate, isophthalate, laurate, linoleate, maleate, mellitate, myristate, octanoate, oleate, palmitate, pelargonate, phosphate, phthalate, ricinoleate, sebacate, stearate, succinate, toluate, tallate, decanoate, or epoxidized vegetable oils, toluamide or chlorinated paraffins, for regulating the controlled release rate and release profile of said bioactive agent, said components being selected so that said complex will remain in an application site for a period of time sufficient to effectively treat a population of one or more terrestrial organisms and wherein said composition is free of superabsorbent polymers.

3. The article of manufacture of claim 1 or 2 wherein said plasticizer is an acetate.

4. The article of manufacture of claim 1 or 2 wherein said plasticizer is an adipate.

5. The article of manufacture of claim 1 or 2 wherein said plasticizer is an azeleate.

6. The article of manufacture of claim 1 or 2 wherein said plasticizer is a benzoate.

7. The article of manufacture of claim 1 or 2 wherein said plasticizer is a caprylamide.

8. The article of manufacture of claim 1 or 2 wherein said plasticizer is a capramide.

9. The article of manufacture of claim 1 or 2 wherein said plasticizer is a caprate.

10. The article of manufacture of claim 1 or 2 wherein said plasticizer is a citrate.

11. The article of manufacture of claim 1 or 2 wherein said plasticizer is a cocoate.

12. The article of manufacture of claim 1 or 2 wherein said plasticizer is a fumarate.

13. The article of manufacture of claim 1 or 2 wherein said plasticizer is a glutarate.

14. The article of manufacture of claim 1 or 2 wherein said plasticizer is a glycolate.

15. The article of manufacture of claim 1 or 2 wherein said plasticizer is a heptanoate.

16. The article of manufacture of claim 1 or 2 wherein said plasticizer is an isobutyrate.

17. The article of manufacture of claim 1 or 2 wherein said plasticizer is an isophthalate.

18. The article of manufacture of claim 1 or 2 wherein said plasticizer is a laurate.

19. The article of manufacture of claim 1 or 2 wherein said plasticizer is a linoleate.

20. The article of manufacture of claim 1 or 2 wherein said plasticizer is a maleate.

21. The article of manufacture of claim 1 or 2 wherein said plasticizer is a mellitate.

22. The article of manufacture of claim 1 or 2 wherein said plasticizer is a myristate.

23. The article of manufacture of claim 1 or 2 wherein said plasticizer is an octanoate.

24. The article of manufacture of claim 1 or 2 wherein said plasticizer is an oleate.

25. The article of manufacture of claim 1 or 2 wherein said plasticizer is a palmitate.

26. The article of manufacture of claim 1 or 2 wherein said plasticizer is a pelargonate.

27. The article of manufacture of claim 1 or 2 wherein said plasticizer is a phosphate.

28. The article of manufacture of claim 1 or 2 wherein said plasticizer is a phthalate.

29. The article of manufacture of claim 1 or 2 wherein said plasticizer is a ricinoleate.

30. The article of manufacture of claim 1 or 2 wherein said plasticizer is a sebacate.

31. The article of manufacture of claim 1 or 2 wherein said plasticizer is a stearate.

32. The article of manufacture of claim 1 or 2 wherein said plasticizer is a succinate.

33. The article of manufacture of claim 1 or 2 wherein said plasticizer is a toluate.

34. The article of manufacture of claim 1 or 2 wherein said plasticizer is a toluamide.

35. The article of manufacture of claim 1 or 2 wherein said plasticizer is a tallate.

36. The article of manufacture of any one of claims 26 or 27 wherein said composition of matter is a product produced by the process of combining the carrier compound, bioactive agent, and organic plasticizer.

37. The Article of manufacture of claim 3 wherein said composition of matter is a product produced by the process of combining the bioactive agent, organic plasticizer and carrier component.

38. The Article of manufacture of claim 4 wherein said composition of matter is a product produced by the process of combining the bioactive agent, organic plasticizer and carrier component.

39. The Article of manufacture of claim 5 wherein said composition of matter is a product produced by the process of combining the bioactive agent, organic plasticizer and carrier component.

40. The Article of manufacture of claim 6 wherein said composition of matter is a product produced by the process of combining the bioactive agent, organic plasticizer and carrier component.

41. The Article of manufacture of claim 7 wherein said composition of matter is a product produced by the process of combining the bioactive agent, organic plasticizer and carrier component.

42. The Article of manufacture of claim 8 wherein said composition of matter is a product produced by the process of combining the bioactive agent, organic plasticizer and carrier component.

43. The Article of manufacture of claim 9 wherein said composition of matter is a product produced by the process of combining the bioactive agent, organic plasticizer and carrier component.

44. The Article of manufacture of claim 10 wherein said composition of matter is a product produced by the process of combining the bioactive agent, organic plasticizer and carrier component.

45. The Article of manufacture of claim 11 wherein said composition of matter is a product produced by the process of combining the bioactive agent, organic plasticizer and carrier component.

46. The Article of manufacture of claim 12 wherein said composition of matter is a product produced by the process of combining the bioactive agent, organic plasticizer and carrier component.

47. The Article of manufacture of claim 13 wherein said composition of matter is a product produced by the process of combining the bioactive agent, organic plasticizer and carrier component.

48. The Article of manufacture of claim 14 wherein said composition of matter is a product produced by the process of combining the bioactive agent, organic plasticizer and carrier component.

49. The Article of manufacture of claim 15 wherein said composition of matter is a product produced by the process of combining the bioactive agent, organic plasticizer and carrier component.

50. The Article of manufacture of claim 16 wherein said composition of matter is a product produced by the process of combining the bioactive agent, organic plasticizer and carrier component.

51. The Article of manufacture of claim 17 wherein said composition of matter is a product produced by the process of combining the bioactive agent, organic plasticizer and carrier component.

52. The Article of manufacture of claim 18 wherein said composition of matter is a product produced by the process of combining the bioactive agent, organic plasticizer and carrier component.

53. The Article of manufacture of claim 19 wherein said composition of matter is a product produced by the process of combining the bioactive agent, organic plasticizer and carrier component.

54. The Article of manufacture of claim 20 wherein said composition of matter is a product produced by the process of combining the bioactive agent, organic plasticizer and carrier component.

55. The Article of manufacture of claim 21 wherein said composition of matter is a product produced by the process of combining the bioactive agent, organic plasticizer and carrier component.

56. The Article of manufacture of claim 22 wherein said composition of matter is a product produced by the process of combining the bioactive agent, organic plasticizer and carrier component.

57. The Article of manufacture of claim 23 wherein said composition of matter is a product produced by the process of combining the bioactive agent, organic plasticizer and carrier component.

58. The Article of manufacture of claim 24 wherein said composition of matter is a product produced by the process of combining the bioactive agent, organic plasticizer and carrier component.

59. The Article of manufacture of claim 25 wherein said composition of matter is a product produced by the process of combining the bioactive agent, organic plasticizer and carrier component.

60. The Article of manufacture of claim 26 wherein said composition of matter is a product produced by the process of combining the bioactive agent, organic plasticizer and carrier component.

61. The Article of manufacture of claim 27 wherein said composition of matter is a product produced by the process of combining the bioactive agent, organic plasticizer and carrier component.

62. The Article of manufacture of claim 28 wherein said composition of matter is a product produced by the process of combining the bioactive agent, organic plasticizer and carrier component.

63. The Article of manufacture of claim 29 wherein said composition of matter is a product produced by the process of combining the bioactive agent, organic plasticizer and carrier component.

64. The Article of manufacture of claim 30 wherein said composition of matter is a product produced by the process of combining the bioactive agent, organic plasticizer and carrier component.

65. The Article of manufacture of claim 31 wherein said composition of matter is a product produced by the process of combining the bioactive agent, organic plasticizer and carrier component.

66. The Article of manufacture of claim 32 wherein said composition of matter is a product produced by the process of combining the bioactive agent, organic plasticizer and carrier component.

67. The Article of manufacture of claim 33 wherein said composition of matter is a product produced by the process of combining the bioactive agent, organic plasticizer and carrier component.

68. The Article of manufacture of claim 34 wherein said composition of matter is a product produced by the process of combining the bioactive agent, organic plasticizer and carrier component.

69. The Article of manufacture of claim 35 wherein said composition of matter is a product produced by the process of combining the bioactive agent, organic plasticizer and carrier component.

* * * * *

UNITED STATES PATENT AND TRADEMARK OFFICE

CERTIFICATE OF CORRECTION

PATENT NO. : 6,335,027 B1
DATED : January 1, 2002
INVENTOR(S) : Richard Levy

It is certified that error appears in the above-identified patent and that said Letters Patent is hereby corrected as shown below:

Column 47,
Line 45, insert "an" before -- acetate --.

Signed and Sealed this

Twenty-first Day of May, 2002

Attest:

JAMES E. ROGAN

*Attesting Officer* *Director of the United States Patent and Trademark Office*

UNITED STATES PATENT AND TRADEMARK OFFICE

CERTIFICATE OF CORRECTION

PATENT NO. : 6,335,027 B1
DATED : January 1, 2002
INVENTOR(S) : Richard Levy

It is certified that error appears in the above-identified patent and that said Letters Patent is hereby corrected as shown below:

Column 49,
Lines 50-51, change "claims 26 or 27" to -- claims 1 or 2 --.

Column 52,
Line 25, add the following claims:

70. The article of manufacture of claim 1 or 2 wherein said plasticizer is a decanoate.

71. The article of manufacture of claim 71 wherein said composition of matter is a product produced by the process of combining the bioactive agent, organic plasticizer and carrier component.

Signed and Sealed this

Sixteenth Day of September, 2003

JAMES E. ROGAN
*Director of the United States Patent and Trademark Office*

UNITED STATES PATENT AND TRADEMARK OFFICE

CERTIFICATE OF CORRECTION

PATENT NO. : 6,335,027 B1
DATED : January 1, 2002
INVENTOR(S) : Richard Levy

It is certified that error appears in the above-identified patent and that said Letters Patent is hereby corrected as shown below:

Column 49,
Lines 50-51, change "claims 26 or 27" to -- claims 1 or 2 --.

Column 52,
Line 25, add the following claims:

70. The article of manufacture of claim 1 or 2 wherein said plasticizer is a decanoate.

71. The article of manufacture of claim 70 wherein said composition of matter is a product produced by the process of combining the bioactive agent, organic plasticizer and carrier component.

This certificate supersedes Certificate of Correction issued September 16, 2003.

Signed and Sealed this

Twentieth Day of April, 2004

JON W. DUDAS
*Acting Director of the United States Patent and Trademark Office*